(12) United States Patent
Yamada

(10) Patent No.: US 7,386,158 B2
(45) Date of Patent: Jun. 10, 2008

(54) APPARATUS FOR SUPPRESSING NOISE BY ADAPTING FILTER CHARACTERISTICS TO INPUT IMAGE SIGNAL BASED ON CHARACTERISTICS OF INPUT IMAGE SIGNAL

(75) Inventor: Masahiko Yamada, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 1150 days.

(21) Appl. No.: 09/978,275

(22) Filed: Oct. 17, 2001

(65) Prior Publication Data
US 2002/0071600 A1 Jun. 13, 2002

(30) Foreign Application Priority Data
Oct. 17, 2000 (JP) .............................. 2000-316235
Oct. 25, 2000 (JP) .............................. 2000-324904

(51) Int. Cl.
*G06K 9/00* (2006.01)
(52) U.S. Cl. ........................ 382/132; 382/261; 382/264
(58) Field of Classification Search ................ 382/132, 382/240, 261, 264, 266, 272, 265
See application file for complete search history.

(56) References Cited

U.S. PATENT DOCUMENTS

| | | | | |
|---|---|---|---|---|
| 5,046,147 A | | 9/1991 | Funahashi et al. | 250/327.2 |
| 5,050,227 A | * | 9/1991 | Furusawa et al. | 382/269 |
| 5,351,305 A | * | 9/1994 | Wood et al. | 382/128 |
| 5,442,462 A | * | 8/1995 | Guissin | 358/463 |
| 5,461,655 A | | 10/1995 | Vuylsteke et al. | 378/62 |
| 5,550,888 A | * | 8/1996 | Neitzel et al. | 378/98.7 |
| 5,708,693 A | * | 1/1998 | Aach et al. | 378/62 |
| 5,717,791 A | * | 2/1998 | Labaere et al. | 382/274 |
| 5,956,427 A | * | 9/1999 | Greenspan et al. | 382/240 |
| 5,991,457 A | | 11/1999 | Ito et al. | 382/254 |
| 6,674,915 B1 | * | 1/2004 | Wang | 382/263 |
| 6,704,437 B1 | * | 3/2004 | He et al. | 382/128 |
| 2002/0094114 A1 | * | 7/2002 | Ogino | 382/128 |

FOREIGN PATENT DOCUMENTS

| | | |
|---|---|---|
| EP | 0610604 A1 | 8/1994 |
| JP | 2000-306089 | 11/2000 |
| JP | 2001-57677 | 2/2001 |
| WO | WO 98/55916 A1 | 12/1998 |

OTHER PUBLICATIONS

Japanese Patent Abstract, 2001-57677.
Japanese Patent Abstract, 2000-306089.

* cited by examiner

*Primary Examiner*—Brian Werner
*Assistant Examiner*—Anthony Mackowey
(74) *Attorney, Agent, or Firm*—Sughrue Mion, PLLC

(57) ABSTRACT

In an apparatus for suppressing noise in an input image signal representing a radiographic image: at least one first characteristic of the input image signal is obtained by calculation based on information indicating an exposure dose with which the radiographic image has been produced; at least one second characteristic of a smoothing filter is adapted to the input image signal based on the at least one first characteristic; and the input image signal is processed by using the smoothing filter so as to smooth the radiographic image. In addition, a plurality of band-limited image signals respectively representing a plurality of band-limited images belonging to a plurality of different frequency bands are generated based on the input image signal, each of the plurality of band-limited image signals is processed by using the smoothing filter so as to smooth each of the plurality of band-limited images.

16 Claims, 10 Drawing Sheets

IMAGE

VECTORS IN FULL-ANGLE REPRESENTATION

VECTORS IN DOUBLE-ANGLE REPRESENTATION

BOLD LINES INDICATE ORIENTATIONS OF LINES

DEFINITION OF DOUBLE-ANGLE REPRESENTATION

FILTER FOR $q_0$

FILTER FOR $q_1$

FILTER FOR $q_2$

FILTER FOR $q_3$

FIG. 9

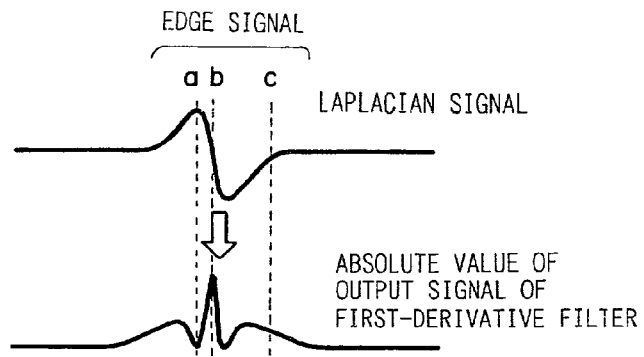

EDGE SIGNAL
a b c
LAPLACIAN SIGNAL

ABSOLUTE VALUE OF
OUTPUT SIGNAL OF
FIRST-DERIVATIVE FILTER

FIG.10A

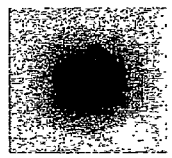

FOR TARGET
RESOLUTION LEVEL

FIG.10B

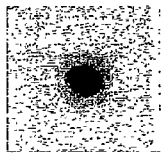

FOR ONE-LEVEL LOWER
RESOLUTION LEVEL

FIG.10C

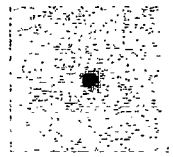

FOR TWO-LEVEL LOWER
RESOLUTION LEVEL

FIG.11A  FIG.11B  FIG.11C  FIG.11D

LINE | LINE/NOISE | INTERSECTION POINT OR END POINT | NOISE
$C \fallingdotseq 1$ & $E \fallingdotseq 1$ | $C \fallingdotseq 1$ & $E << 1$ | $C << 1$ & $E \fallingdotseq 1$ | $C << 1$ & $E << 1$

APPARATUS FOR SUPPRESSING NOISE BY ADAPTING FILTER CHARACTERISTICS TO INPUT IMAGE SIGNAL BASED ON CHARACTERISTICS OF INPUT IMAGE SIGNAL

CROSS-REFERENCE TO RELATED APPLICATION

The subject matters disclosed in this specification are related to the subject matters disclosed in the following patents and patent applications:

(i) U.S. Ser. No. 09/592,602, (now U.S. Pat. No. 6,754, 398) filed by Masahiko Yamada (the inventor of the present patent application) on Jun. 12, 2000 and entitled "Method of and System for Image Processing and Recording Medium for Carrying Out the Method" corresponding to Japanese Patent Application No. 11(1999)-363766, which is disclosed in Japanese Unexamined Patent Publication No. 2001-57677

(ii) U.S. Ser. No. 09/505,768, (now U.S. Pat. No. 6,771, 793) filed by Masahiko Yamada (the inventor of the present patent application) on Feb. 17, 2000 and entitled "Image Processing Method and Apparatus" corresponding to Japanese Patent Application No. 2000-022828, which is disclosed in Japanese Unexamined Patent Publication No. 2000-306089

(iii) U.S. Pat. No. 5,046,147, granted to Takashi Funabashi et al. on Sep. 3, 1991 and entitled "Radiation Image Processing Method" corresponding to Japanese Patent Application No. 63(1989)-261174, which is disclosed in Japanese Unexamined Patent Publication No. 2(1990)-108175

(iv) U.S. Pat. No. 5,991,457, granted to Masahiko Yamada (the inventor of the present patent application) and Wataru Ito on Nov. 23, 1999 and entitled "Multi-resolution Transforming, Image Processing and Dynamic Range Compressing Method and Apparatus" corresponding to Japanese Patent Application No. 8(1996)-182156, which is disclosed in Japanese Unexamined Patent Publication No. 10(1998)-75364.

The contents of the above U.S. patent applications and U.S. patents and the corresponding Japanese Patent Applications are incorporated in this specification by reference.

BACKGROUND OF THE INVENTION

1. Field of the Invention

The present invention relates to a method and an apparatus for suppressing noise included in an image signal representing a radiographic image. The present invention also relates to a method for suppressing noise included in an image signal representing a radiographic image. The present invention further relates to a computer-readable storage medium storing a program which instructs a computer to execute a method for suppressing noise included in an image signal representing a radiographic image.

2. Description of the Related Art

Currently, when radiographic images obtained by computed radiography (CR) or the like are used in diagnosis, image processing such as frequency emphasis processing or gradation processing is performed on the radiographic images before the radiographic images are displayed on CRT monitors as soft copies or recorded in films as hard copies.

Generally, radiographic images tend to include undesirably noticeable quantization noise in low density areas corresponding to low-intensity radiation exposure. Therefore, various methods have been proposed for suppressing noise components included in image signals carrying radiographic images.

For example, U.S. Pat. No. 5,461,655 (corresponding to Japanese Unexamined Patent Publications No. 6(1994)-96200) discloses a method for suppressing noise components in an image. In the method disclosed in U.S. Pat. No. 5,461,655, an image is transformed (decomposed) into a set of detail images (represented by band-limited image signals corresponding to 1 to M resolution levels). Then, a moving average of squared pixel values of each detail image in an N×N neighborhood centered around each pixel of interest (i.e., a sum of the squared pixel values divided by $N^2$) is calculated as a local variance, and a histogram of the local variance is produced for each detail image. Next, a local variance corresponding to the peak in the histogram is obtained as a noise variance, and the local variance corresponding to each pixel is compared with the noise variance. When the local variance is comparable to or smaller than the noise variance, a portion of the band-limited image signal corresponding to the pixel is reduced. Thereafter, the set of detail images processed as above are inversely transformed (composed) to the space of the original image by inverse multiresolution transformation so that an image in which the noise is suppressed is obtained.

U.S. Pat. No. 5,461,655 also discloses that noise variances for detail images at lower resolution levels can be calculated based on a noise variance for a detail image at the highest resolution level, i.e., the finest-grained detail image.

According to the method disclosed in U.S. Pat. No. 5,461,655, noise is suppressed by using a noise variance obtained from local variances of each detail image and a histogram of the local variances, based on the assumption that the noise is uniformly distributed in the entire image. However, noise in actual radiographic images is not uniformly distributed. For example, noise levels are relatively high in areas in which images of objects exist, and noise levels are relatively low in areas in which images of objects do not exist. Therefore, when the method disclosed in U.S. Pat. No. 5,461,655 is applied to the actual radiographic images, edge information in the areas in which the noise levels are low is suppressed as well as the noise. That is, edge degradation occurs, and sharpness of the radiographic images decreases. Consequently, in practice, it is not possible to sufficiently suppress the noise in the areas in which the noise levels are high, by the method to disclosed in U.S. Pat. No. 5,461,655, since noise is suppressed by using the threshold value obtained from the histogram according to the method.

In addition, shapes of histograms obtained from radiographic images including images of objects having complex structures are different from shapes of histograms obtained from radiographic images including images of objects having simple structures, even when the average noise levels in the images of objects having the complex structures and those having the simple structures are almost identical. Therefore, it is difficult to desirably discriminate between edges and noise according to variations between objects.

SUMMARY OF THE INVENTION

An object of the present invention is to provide an apparatus for effectively suppressing noise in or eliminating noise from a radiographic image regardless of an exposure dose with which the radiographic image has been produced, and reducing edge degradation which is likely to be caused by noise suppression in a noisy radiographic image.

Another object of the present invention is to provide a method for effectively suppressing noise in or eliminating noise from a radiographic image regardless of an exposure dose with which the radiographic image has been produced, and reducing edge degradation which is likely to be caused by noise suppression in a noisy radiographic image.

A further object of the present invention is to provide a computer-readable storage medium storing a program which instructs a computer to execute a method for effectively suppressing noise in or eliminating noise from a radiographic image regardless of an exposure dose with which the radiographic image has been produced, and reducing edge degradation which is likely to be caused by noise suppression in a noisy radiographic image.

(1) According to the first aspect of the present invention, there is provided an apparatus for suppressing noise in an input image signal representing a radiographic image, comprising: a smoothing unit which processes the input image signal by using a smoothing filter so as to smooth the radiographic image; and a characteristic calculation unit which obtains at least one first characteristic of the input image signal by calculation based on first information indicating an exposure dose with which the radiographic image has been produced; the smoothing unit adapts at least one second characteristic of the smoothing filter to the input image signal based on the at least one first characteristic of the input image signal.

The information indicating an exposure dose with which the radiographic image has been produced may be information which directly indicates the exposure dose with which the radiographic image has been produced or information which indirectly indicates the exposure dose with which the radiographic image has been produced (i.e., information corresponding to the exposure dose with which the radiographic image has been produced) The information which directly indicates the exposure dose with which the radiographic image has been produced is, for example, Information from a photo-timer. The information which indirectly indicates the exposure dose with which the radiographic image has been produced is, for example, information indicating a menu of radiography, an age of a patient, a condition of radiography (e.g., a condition for irradiation by a radiographic apparatus), a normalization condition (as disclosed in U.S. Pat. No. 5,046,147 corresponding to Japanese Unexamined Patent Publication No. 2(1990)-108175), or a pixel value (density value) of the radiographic image.

When the apparatus according to the first aspect of the present invention is used, a radiographic image in which noise is effectively suppressed or eliminated can be obtained regardless of the exposure dose with which the original radiographic image has been produced.

Preferably, the apparatus according to the first aspect of the present invention may also have one or any possible combination of the following additional features (i) to (v)

(i) The apparatus according to the first aspect of the present invention may further comprise a band-limited-image-signal generation unit which generates a plurality of band-limited image signals respectively representing a plurality of band-limited images belonging to a plurality of different frequency bands, based on the input image signal, the smoothing unit processes the plurality of band-limited image signals by using the smoothing filter so as to smooth each of the plurality of band-limited images.

In this case, it is possible to reconstruct a radiographic image from the plurality of band-limited image signals after noise suppression or elimination is performed in each of the plurality of band-limited image signals. That is, a radiographic image in which noise is effectively suppressed or eliminated can be obtained regardless of the exposure dose with which the original radiographic image has been produced.

(ii) In the apparatus having the feature of (i), the band-limited-image-signal generation unit may generate the plurality of band-limited image signals by performing multiresolution decomposition of the input image signal. The multiresolution transformation is, for example, the Laplacian pyramid decomposition or wavelet transformation.

In this case, after noise in the plurality of band-limited image signals is suppressed, a noise-suppressed image can be reconstructed by inverse multiresolution development (transformation). Thus, a radiographic image in which noise is effectively suppressed or eliminated can be obtained regardless of the exposure dose with which the original radiographic image has been produced.

Further, when the plurality of band-limited image signals are generated from the input image signal by multiresolution decomposition, the generation of the plurality of band-limited image signals and the reconstruction of the noise-suppressed image can be performed in a short time. Therefore, the overall throughput of the noise suppression processing can be increased.

(iii) In the apparatus having the feature of (i), the at least one first characteristic of the input image signal can be calculated based on other (second) information as well as the aforementioned first information indicating the exposure dose with which the radiographic image has been produced. For example, the above second information may be information which is locally calculated from pixel values in a neighborhood of the pixel of interest. That is, in the apparatus having the feature of (i), the characteristic calculation unit may obtain the at least one first characteristic of the input image signal based on second information which is locally calculated from pixel values in a neighborhood of a pixel of interest in at least one of the plurality of band-limited images represented by at least one of the plurality of band-limited image signals, as well as the first information.

The above second information may be any information based on which a degree of edge confidence can be determined. For example, the second information may be a local average (e.g., a moving average) of vectors or density values or a local sum of squared density values (e.g., a local variance).

When the at least one first characteristic of the input image signal includes the above second information as well as the first information, the at least one second characteristic of the smoothing filter can be adapted to the input image signal substantially based on a degree of edge confidence as well as the exposure dose with which the radiographic image has been produced. Therefore, it is possible to more easily discriminate between edges and noise according to noise variations depending on location in the radiographic image. Thus, a radiographic image in which edge degradation is reduced and noise is effectively suppressed can be obtained.

(iv) In the apparatus having the feature of (iii), the characteristic calculation unit may obtain a pixel vector at the pixel of interest in the at least one of the plurality of band-limited images, and detect an orientation of an edge as the second information. In this case, the smoothing unit can adapt the at least one second characteristic of the smoothing filter to the input image signal so that the radiographic image is smoothed along the orientation of the edge.

According to the apparatus having the feature of (iv), the edge degradation, which is likely to be caused by noise suppression in a noisy image, can be reduced. In addition, variations in image quality due to variations in the exposure dose can be suppressed. Further, since the smoothing processing can be performed along the orientation of the edge, noise on the edge can be appropriately suppressed without reducing edge contrast. In other words, the edge can be retained even when the noise suppression is performed.

(v) The smoothing filter may include for each of a plurality of predetermined directions a plurality of filters respectively smoothing the radiographic image in the predetermined direction to a plurality of different degrees. In this case, the smoothing unit can adapt the at least one second characteristic of the smoothing filter to the input image signal by selecting one of the plurality of filters based on the at least one first characteristic of the input image signal.

According to the apparatus having the feature of (v), processing for noise suppression can be performed in a short time. Therefore, the overall throughput of the processing can be increased.

(2) According to the second aspect of the present invention, there is provided a method for suppressing noise in an input image signal representing a radiographic image, the method comprising the steps of: (a) obtaining at least one first characteristic of the input image signal by calculation based on information indicating an exposure dose with which the radiographic image has been produced; (b) adapting at least one second characteristic of a smoothing filter to the input image signal based on the at least one first characteristic of the input image signal; and (c) processing the input image signal by using the smoothing filter so as to smooth the radiographic image.

The method of suppressing noise according to the second aspect of the present invention can be executed by a computer. In this case, it is possible to store in a computer-readable storage medium a program which makes the computer execute the method of suppressing noise according to the second aspect of the present invention.

That is, according to the third aspect of the present invention, there is provided a computer-readable storage medium storing a program which instructs a computer to execute a method for suppressing noise in an input image signal representing a radiographic image, the method comprising the steps of: (a) obtaining at least one first characteristic of the input image signal by calculation based on information indicating an exposure dose with which the radiographic image has been produced; (b) adapting at least one second characteristic of a smoothing filter to the input image signal based on the at least one first characteristic of the input image signal; and (c) processing the input image signal by using the smoothing filter so as to smooth the radiographic image.

According to the fourth aspect of the present invention, there is provided a method for suppressing noise in an input image signal representing a radiographic image, the method comprising the steps of: (a) generating a plurality of band-limited image signals respectively representing a plurality of band-limited images belonging to a plurality of different frequency bands, based on the input image signal; (b) obtaining at least one first characteristic of the input image signal by calculation based on information indicating an exposure dose with which the radiographic image has been produced; (c) adapting at least one second characteristic of a smoothing filter to the input image signal based on the at least one first characteristic of the input image signal; and (d) processing the plurality of band-limited image signals by using the smoothing filter so as to smooth each of the plurality of band-limited images.

The method of suppressing noise according to the fourth aspect of the present invention can be executed by a computer. In this case, it is possible to store in a computer-readable storage medium a program which makes the computer execute the method of suppressing noise according to the fourth aspect of the present invention.

That is, according to the fifth aspect of the present invention, there is provided a computer-readable storage medium storing a program which instructs a computer to execute a method for suppressing noise in an input image signal representing a radiographic image, the method comprising the steps of: (a) generating a plurality of band-limited image signals respectively representing a plurality of band-limited images belonging to a plurality of different frequency bands, based on the input image signal; (b) obtaining at least one first characteristic of the input image signal by calculation based on information indicating an exposure dose with which the radiographic image has been produced; (c) adapting at least one second characteristic of a smoothing filter to the input image signal based on the at least one first characteristic of the input image signal; and (d) processing the plurality of band-limited image signals by using the smoothing filter so as to smooth each of the plurality of band-limited images.

When the method according to the second or fourth aspect of the present invention or the computer-readable storage medium according to the third or fifth aspect of the present invention is used, the at least one first characteristic of the input image signal is calculated based on the information indicating the exposure dose with which the (original) radiographic image has been produced, and the at least one second characteristic of the smoothing filter is adapted to the input image signal based on the at least one first characteristic of the input image signal. Therefore, it is possible to obtain a radiographic image in which noise is effectively suppressed or eliminated regardless of the exposure dose with which the original radiographic image has been produced.

(3) According to the sixth aspect of the present invention, there is provided an apparatus for suppressing noise in an input image signal representing a radiographic image, comprising: a band-limited-image-signal generation unit which generates a plurality of band-limited image signals respectively representing a plurality of band-limited images belonging to a plurality of different frequency bands, based on the input image signal; an index-value obtaining unit which obtains at least one index value indicating a degree of suppression of the noise, based on information indicating an exposure dose with which the radiographic image has been produced; and a noise suppression unit which processes each of the plurality of band-limited image signals so as to suppress noise in each of the plurality of band-limited images based on the at least one index value.

The at least one index value indicating a degree of suppression of the noise may be any value which can indicate a degree of suppression of the noise included in the radiographic image. For example, information indicating the exposure dose per se can be used as the at least one index value.

When the apparatus according to the sixth aspect of the present invention is used, at least one index value indicating a degree of suppression of the noise is obtained based on information indicating an exposure dose with which the radiographic image has been produced, and each of a plurality of band-limited image signals is processed so as to suppress noise in each of the plurality of band-limited images based on the at least one index value. Therefore, when a radiographic image is reconstructed from the plurality of band-limited image signals after noise suppression or elimination is performed in each of the plurality of band-limited image signals, a radiographic image in which noise is effectively suppressed or eliminated can be obtained regardless of the exposure dose with which the original radiographic image has been produced.

Preferably, the apparatus according to the sixth aspect of the present invention may also have one or any possible combination of the following additional features (vi) to (xiii).

(vi) The index-value obtaining unit may obtain the at least one index value indicating the degree of suppression of the noise for each of the plurality of band-limited image signals, and the noise suppression unit may process each of the plurality of band-limited image signals so as to suppress the noise in each of the plurality of band-limited images based on the at least one index value obtained for one of the plurality of band-limited image signals representing the band-limited image.

In this case, each frequency component of the input image signal can be processed by using at least one optimum index value obtained for each of the plurality of frequency bands. Therefore, fine-grained noise suppression can be performed.

(vii) The index-value obtaining unit may obtain the at least one index value indicating the degree of suppression of the noise for each pixel of each of the plurality of band-limited images, and the noise suppression unit may process each of the plurality of band-limited image signals so as to suppress noise in the pixel of each of the plurality of band-limited images based on the at least one index value obtained for the pixel of the band-limited image.

In this case, each portion of each frequency component (band-limited image) of the radiographic image can be processed by using at least one optimum index value obtained for the pixel of the band-limited image. Since the at least one optimum index value can be obtained according to variations depending on location in the radiographic image, more fine-grained noise suppression can be performed than that can be performed in the case where the at least one index value is obtained from the entire image.

(viii) In the apparatus having the feature of (vii), the index-value obtaining unit may obtain a first evaluation value from a first one of the plurality of band-limited image signals belonging to a first one of the plurality of different frequency bands and a second evaluation value from a second one of the plurality of band-limited image signals belonging to a second one of the plurality of different frequency bands which is lower than the first one of the plurality of different frequency bands, determine weights based on the information indicating the exposure dose with which the radiographic image has been produced, for use in a weighted sum of the first and second evaluation values, obtain the weighted sum, and obtain based on the weighted sum the at least one index value indicating the degree of suppression of the noise for the first one of the plurality of band-limited image signals.

In this case, the processing for suppressing noise can be performed by using at least one appropriate index value which is determined in consideration of both of noise and edges.

(ix) In the apparatus having the feature of (viii), the index-value obtaining unit may obtain each of the first and second evaluation values for each pixel of the corresponding one of the plurality of band-limited images, based on pixel values of the corresponding one of the plurality of band-limited images in a neighborhood of the pixel.

When the radiographic image is noisy, edge degradation is likely to occur in the noise-suppressed image since the noise-suppressed image is obtained by using the first and second evaluation values which are affected by the noise. However, when the first and second evaluation values are obtained based on pixel values for each pixel of the corresponding one of the plurality of band-limited images in a neighborhood of the pixel, substantially, information in a lower frequency band in which the signal-to-noise ratio is increased is used for obtaining the first and second evaluation values. Therefore, the capability of discrimination between noise and edges is increased, and thus the edge degradation can be reduced.

(x) In the apparatus having the feature of (viii), the index-value obtaining unit may obtain as each of the first and second evaluation values a pixel vector at each pixel of the corresponding one of the plurality of band-limited images, and obtain the at least one index value based on at least one of a length and an orientation of the pixel vector.

In this case, noise can be suppressed more effectively by using the at least one index value including information on characteristics (an orientation and sharpness) of the edge. Therefore, the edge degradation, which is likely to be caused by noise suppression in a noisy radiographic image, can be reduced. Further, variations in image quality due to variations in the exposure dose can be suppressed.

(xi) In the apparatus having the feature of (x), the index-value obtaining unit may obtain as the at least one index value at least one of a degree of edge confidence, an amount of pixel energy, and a vector orientation.

In this case, noise on an edge can be effectively suppressed. Further, when all of the degree of edge confidence, the amount of pixel energy, and the orientation of the pixel vector are used as the at least one index value, the noise on the edge can be further effectively suppressed without reducing edge contrast.

(xii) In the apparatus having the feature of (x), the noise suppression unit may process one of the plurality of band-limited image signals so as to generate a transformed image signal, and obtain a weighted sum of the one of the plurality of band-limited image signals and the transformed image signal by using weights determined based on the at least one index value.

In this case, it is possible to discriminate between noise and edges and appropriately suppress noise in consideration of both of noise and edges.

(xiii) In the apparatus having the feature of (xii), the index-value obtaining unit may obtain a pixel vector at each pixel of one of the plurality of band-limited images, and the noise suppression unit may arrange an orientation-dependent filter based on a length and an orientation of the pixel vector, and obtain the transformed image signal by convolution of pixel values in a neighborhood of the pixel in the band-limited image with the orientation-dependent filter.

In this case, discrimination between noise and edges becomes more accurate, and the overall throughput of the processing for suppressing noise can be increased.

(4) According to the seventh aspect of the present invention, there is provided a method for suppressing noise in an input image signal representing a radiographic image, the method comprising the steps of: (a) generating a plurality of band-limited image signals respectively representing a plurality of band-limited images belonging to a plurality of different frequency bands, based on the input image signal; (b) obtaining at least one index value indicating a degree of suppression of the noise, based on information indicating an exposure dose with which the radiographic image has been produced; and (c) processing each of the plurality of band-limited image signals so as to suppress noise in each of the plurality of band-limited images based on the at least one index value.

The method of suppressing noise according to the seventh aspect of the present invention can be executed by a computer. In this case, it is possible to store in a computer-readable storage medium a program which makes the computer execute the method of suppressing noise according to the second aspect of the present invention.

That is, according to the eighth aspect of the present invention, there is provided a computer-readable storage medium storing a program which instructs a computer to execute a method for suppressing noise in an input image signal representing a radiographic image, the method comprising the steps of: (a) generating a plurality of band-limited image signals respectively representing a plurality of band-limited images belonging to a plurality of different frequency bands, based on the input image signal; (b) obtaining at least one index value indicating a degree of suppression of the noise, based on information indicating an exposure dose with which the radiographic image has been produced; and (c) processing each of the plurality of band-limited image signals so as to suppress noise in each of the plurality of band-limited images based on the at least one index value.

When the method according to the seventh aspect of the present invention or the computer-readable storage medium according to the eighth aspect of the present invention is used, at least one index value indicating a degree of suppression of the noise is obtained based on information indicating an exposure dose with which the radiographic image has been produced, and each of a plurality of band-limited image signals is processed so as to suppress noise in each of the plurality of band-limited images based on the at least one index value. Therefore, when a radiographic image is reconstructed from the plurality of band-limited image signals after noise suppression or elimination is performed in each of the plurality of band-limited image signals, a radiographic image in which noise is effectively suppressed or eliminated can be obtained regardless of the exposure dose with which the original radiographic image has been produced.

DESCRIPTION OF THE DRAWINGS

FIG. 9 is a diagram illustrating a relationship between a Laplacian signal and an output of a first-derivative filter (the absolute value of the first-derivative of the Laplacian signal).

FIGS. 10A to 10C are diagrams respectively illustrating isotropic two-dimensional filters for use in calculation of neighborhood averages of the vector components q0 to q3 at each pixel.

FIGS. 11A to 11D are diagrams respectively illustrating examples of recognition of a line, a point of intersection, an end point, and noise based on a degree C of edge confidence and an index E of pixel energy.

DESCRIPTION OF PREFERRED EMBODIMENTS

Embodiments of the present invention are explained in detail below with reference to drawings.

Construction of Present Invention

Figure 1:
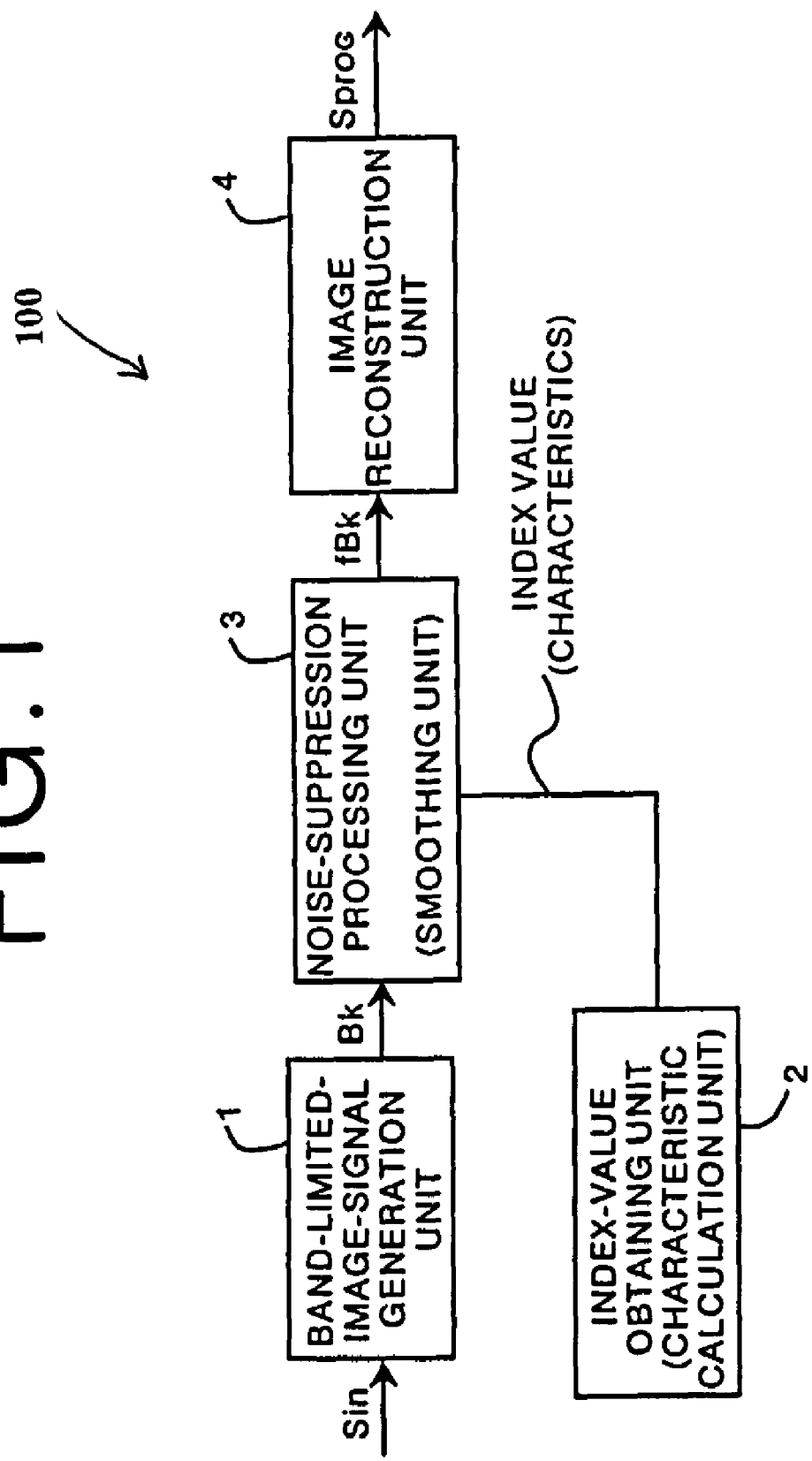
FIG. 1 is a diagram illustrating an outline of a construction of a noise suppressing apparatus according to the present invention.

FIG. 1 is a diagram illustrating an outline of a construction of a noise suppressing apparatus according to the present invention. The noise suppressing apparatus 100 of FIG. 1 comprises a band-limited-image-signal generation unit 1, an index-value obtaining unit 2, a noise-suppression processing unit 3, and an image reconstruction unit 4.

The band-limited-image-signal generation unit 1 receives an input image signal Sin, and generates a plurality of band-limited image signals Bk (k=1 to n) based on the input image signal Sin. The input image signal Sin represents a radiographic image which is obtained by an image reading device or the like, and has a certain resolution. In addition, the plurality of band-limited image signals represent a plurality of band-limited images respectively belong to a plurality of different frequency bands. The index-value obtaining unit 2 obtains at least one index value which indicates a degree of noise suppression based on information indicating an exposure dose with which the radiographic image has been produced. The noise-suppression processing unit 3 performs noise suppression processing on each of the plurality of band-limited image signals according to the degrees of noise suppression. The image reconstruction unit 4 composes (reconstructs) a processed image signal Sproc which represents a noise-suppressed radiographic image, from the plurality of band-limited image signals on which the noise suppression processing is performed by the noise-suppression processing unit 3.

The index-value obtaining unit 2 corresponds to the characteristic calculation unit in the first aspect of the present invention or the index-value obtaining unit in the sixth aspect of the present invention. That is, the index-value obtaining unit 2 obtains a pixel vector at each pixel of interest in each of the plurality of band-limited images, and detects an orientation of an edge as a (noise) characteristic of each of the plurality of band-limited images by using the pixel vector.

The noise-suppression processing unit 3 corresponds to the aforementioned smoothing unit in the first or sixth aspect of the present invention. That is, the noise-suppression processing unit 3 adapts characteristics of smoothing filters to the input image signal so that smoothing processing is performed along the orientation of the edge detected by the index-value obtaining unit 2 on each of the plurality of band-limited image signals Bk.

The input image signal Sin, on which the above noise suppression processing is to be performed, is obtained, for example, by a radiographic-image-information recording-and-reproducing system as disclosed in Japanese Unexamined Patent Publication Nos. 55(1980)-12429 and 56(1981)-11395. In the radiographic-image-information recording-and-reproducing system, a radiographic image of a human body is recorded in a stimulable phosphor sheet, and is then read as a digital image signal by laser beam scanning. The laser beam scanning is performed in two dimensions by moving a laser beam on the stimulable phosphor sheet in a main scanning (lateral) direction while moving the stimulable phosphor sheet in a feeding (longitudinal) direction.

Operations of Apparatus 100

The operations of the 100 are explained below.

Figure 2:
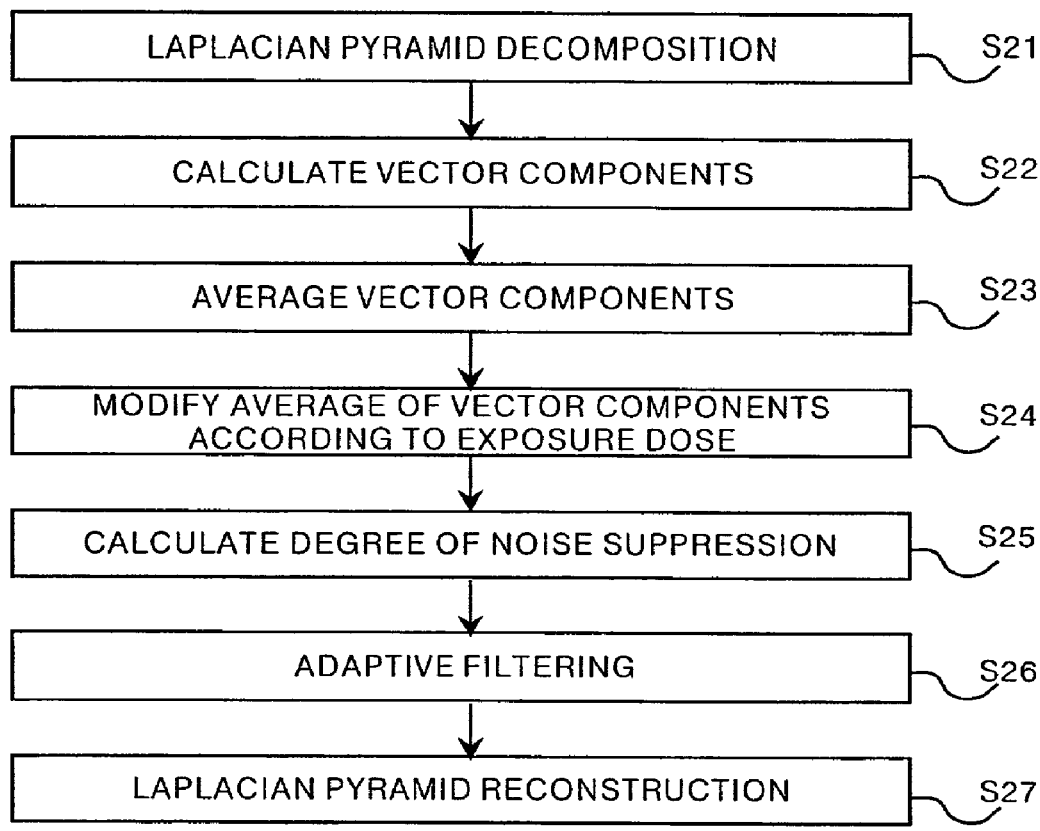
FIG. 2 is a flow diagram illustrating an outline of a sequence of operations of the noise suppressing apparatus 100.

FIG. 2 is a flow diagram illustrating an outline of a sequence of operations of the noise suppressing apparatus 100.

In order to generate the plurality of band-limited image signals, it is preferable to use the so-called multiresolution transformation such as the Laplacian pyramid decomposition or the wavelet transformation. The Laplacian pyramid decomposition is proposed in U.S. Pat. Nos. 5,467,404 and 5,461,655 (respectively corresponding to Japanese Unexamined Patent Publication Nos. 5(1993)-244508 and 6(1994)-096200) and Japanese Unexamined Patent Publication Nos. 2001-057677 and 2000-306089 (respectively corresponding to the copending, coassigned U.S. Ser. Nos. 09/592,602 (now U.S. Pat. No. 6,754,398) and 09/505,768) (now U.S. Pat. 6,771,793), where JUPP Nos. 2001-057677 and 2000-306089 are assigned to the assignee of the present invention. The wavelet transformation is proposed in Japanese Unexamined Patent Publication Nos. 6(1994)-274615 and 2001-057677. Japanese Unexamined Patent Publication Nos. 6(1994)-274615 is also assigned to the assignee of the present invention. Alternatively, the plurality of band-limited image signals may be generated by using other known methods. For example, the plurality of band-limited image signals may be generated by using the unsharp mask signals as disclosed in U.S. Pat. No. 5,991,457 (corresponding to Japanese Unexamined Patent Publication No. 10(1998)-75364, which is assigned to the assignee of the present invention).

In the examples explained below, the Laplacian pyramid decomposition is used for generating the plurality of band-limited image signals.

Thus, in step S21 of FIG. 2, the plurality of band-limited image signals are generated. Then, in step S22, vector components at each pixel position of each of a plurality of band-limited images in multiresolution spaces are calculated, where the plurality of band-limited images are respectively represented by the plurality of band-limited image signals. The vector components obtained in step S22 correspond to the aforementioned first and second evaluation values in the sixth aspect of the present invention. When the vector components are obtained in double-angle representation (which is explained later), four-orientation vector components, i.e., vector components corresponding to four orientations at intervals of 45 degrees, are obtained in each pixel position. In this case, it is possible to discriminate between noise components and edge components in each pixel position by using the four-orientation vector components.

When a singular point (local noise) exists, e.g., when a vector which is extremely greater than surrounding vectors exists, the local noise at each pixel position is likely to be incorrectly recognized as an edge signal. Therefore, in step S23, a neighborhood average (vector average), i.e., an average of values of each vector component in the neighborhood, is obtained by using a one-dimensional filter. This operation is based on an assumption that edge signals are continuous. In this embodiment, the neighborhood average is obtained by using an isotropic two-dimensional space filter, and the neighborhood average (vector average) is modified in step S24 by using a vector component obtained at a resolution level lower than the resolution level at which the neighborhood average is obtained. At this time, the modification of the vector average is made based on information on the exposure dose with which the original radiographic image has been produced.

Next, in step S25, a degree C of edge confidence and an index E of pixel energy are calculated based on each vector modified as above in accordance with a method explained later. Each of the degree C of edge confidence and the index E of pixel energy is an example of the aforementioned at least one index value indicating a degree of suppression of the noise in the sixth to eighth aspects of the present invention. Then, in step S26, noise suppression processing using adaptive filtering is performed based on the degree C of edge confidence and the index E of pixel energy. Finally, in step S27, Laplacian pyramid reconstruction as an example of the aforementioned inverse multiresolution transformation is made so that a processed image in which noise is suppressed is obtained.

The adaptive filtering in step S26 is performed by an anisotropic filter (orientation-dependent filter) and an isotropic filter (orientation-independent filter). It is possible to calculate tens of different sets of anisotropic filter coefficients for the anisotropic filter in advance, and select one of the tens of different sets according to a vector orientation D and an amount of noise. On the other hand, the isotropic filter can be realized by a simple non-linear transformation.

In addition, when an isotropic filter is produced, first, a filter coefficient at the center of a mask is placed at one, and the other filter coefficients are calculated in accordance with the following equation (1) Then, the filter coefficients are normalized so that the sum of the filter coefficients is equal to one.

$$F_{i,j} = \exp\{-\pi \times u(x) \times (i^2 + j^2)/(N \times N \times 2)\} - \\ N \le i \le N \text{ and } -N \le j \le N \qquad (1)$$

On the other hand, the filter coefficients of the anisotropic filter are calculated in accordance with the following equations (2). Then, the filter coefficients of the anisotropic filter are normalized so that the sum of the filter coefficients is equal to one.

$$X_{i,j} = ([\cos\{\cos^{-1}(i/sqrt(i^2 + j^2))deg\}])^2 - \\ N \le i \le N - N \le j \le N \\ Y_{i,j} = X^{u(x)} \times F_{i,j}$$

(2)

In the set of equations (2), deg denotes an angle from a vector orientation.

Next, details of the operations performed in the sequence of FIG. 2 are explained below.

Generation of Band-Limited-Image Signals

Figure 3:
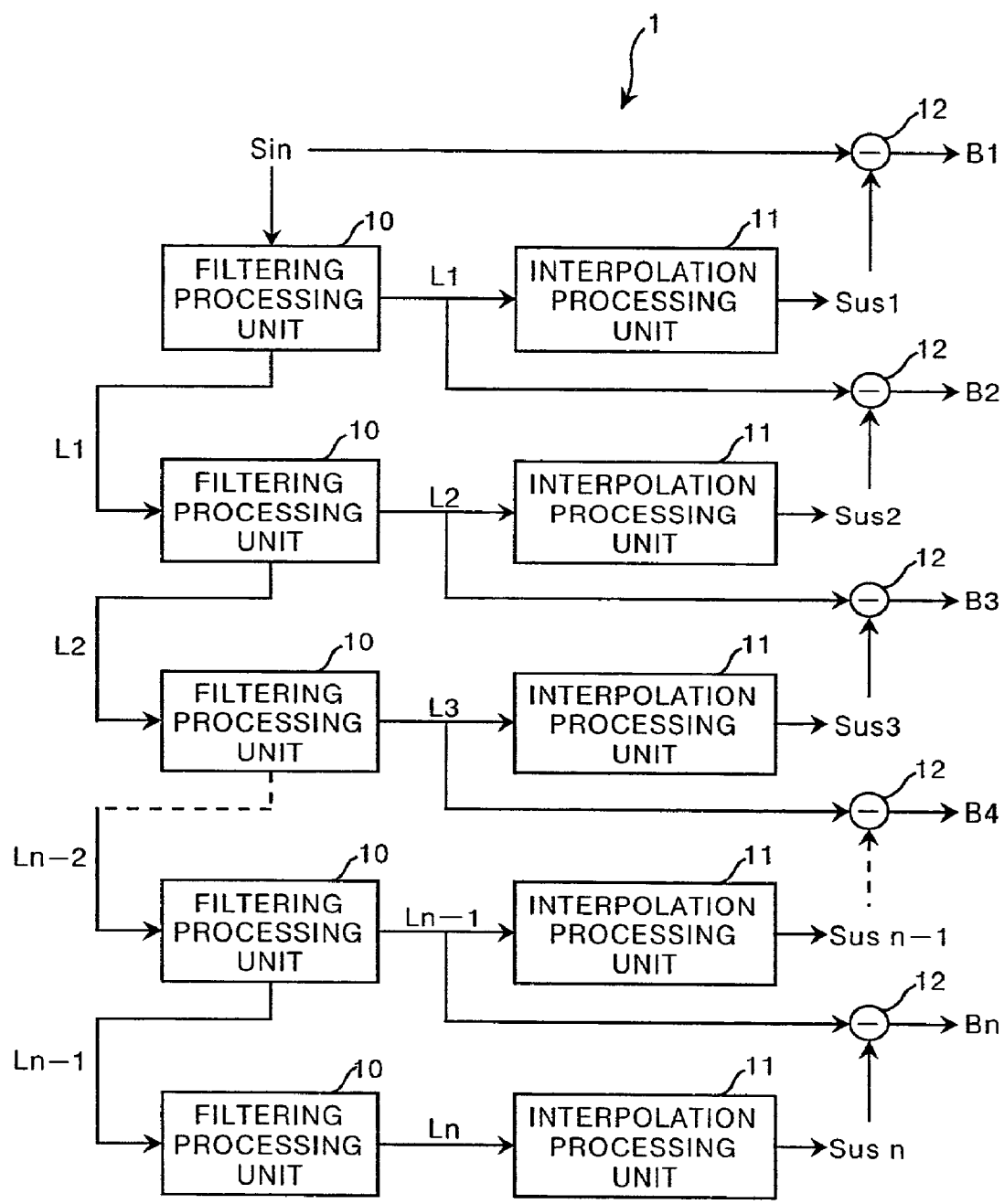
FIG. 3 is a block diagram illustrating an outline of a construction of the band-limited-image-signal generation unit 1.

FIG. 3 is a block diagram illustrating an outline of a construction of the band-limited-image-signal generation unit 1.

As illustrated in FIG. 3, the band-limited-image-signal generation unit 1 comprises, in each stage corresponding to a resolution level, a filtering processing unit 10, an interpolation processing unit 11, is and a subtractor 12. As disclosed in U.S. Pat. No. 5,467,404 (corresponding to Japanese Unexamined Patent Publication No. 5(1993)-244508), the filtering processing unit 10 performs filtering processing on the input image signal Sin in each of the main scanning and feeding directions so as to produce a lower resolution signal L1, which belongs to a lower resolution level than the resolution level of the input image signal Sin. Then, the filtering processing unit 10 performs filtering processing on the lower resolution signal L1 in each of the main scanning and feeding directions so as to produce a next lower resolution signal L2. Thereafter, further lower resolution signals Lk (k=3 to n) are successively obtained by repeating the filtering processing in a similar manner.

Next, the interpolation processing unit 11 performs interpolation processing on each of the lower resolution signals Lk (k=2 to n) so that the number of pixels in each of the main scanning and feeding directions is doubled, i.e., the number of pixels in the lower resolution signal Lk is increased by a factor of four. Thus, a plurality of unsharp image signals Susk (k=1 to n) each having a different degree of sharpness are obtained. Thereafter, the subtractor 12 obtains a difference between each of the lower resolution signal Lk-1 and one of the plurality of unsharp image signals Susk having the same number of pixels as the lower resolution signal Lk-1 so as to generate one of the band-limited image signals Bk.

Figure 4:
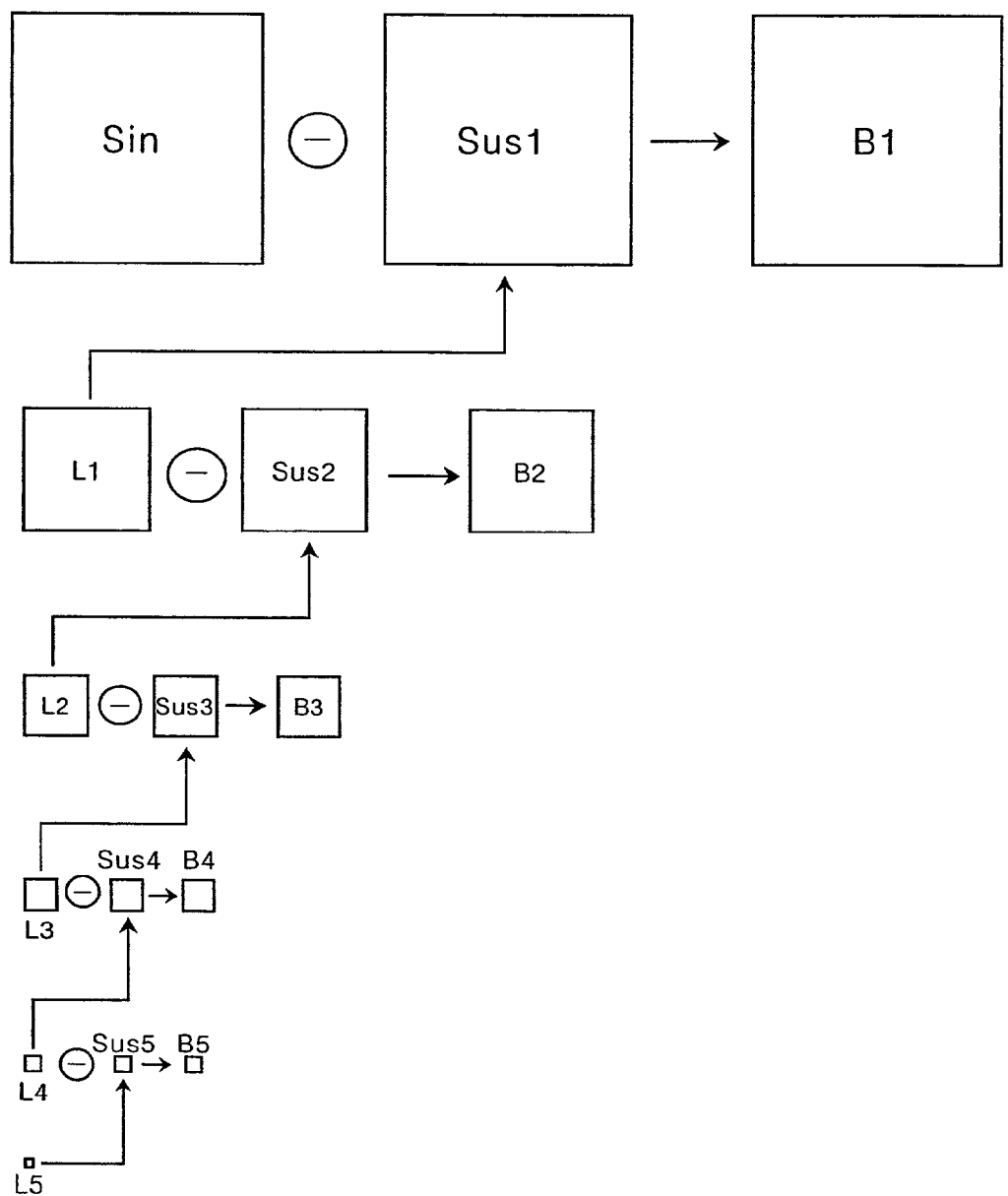
FIG. 4 is a diagram schematically illustrating the above operations of generating five band-limited image signals corresponding to five resolution levels.

Examples of the above operations of generating a plurality of band-limited image signals are schematically illustrated in FIG. 4 for the case where the number of the resolution levels is five.

Operations for Noise Suppression

Details of the operations performed for obtaining at least one index value indicating a degree of noise suppression, and suppressing noise by using the at least one index value are explained below.

Figure 5:
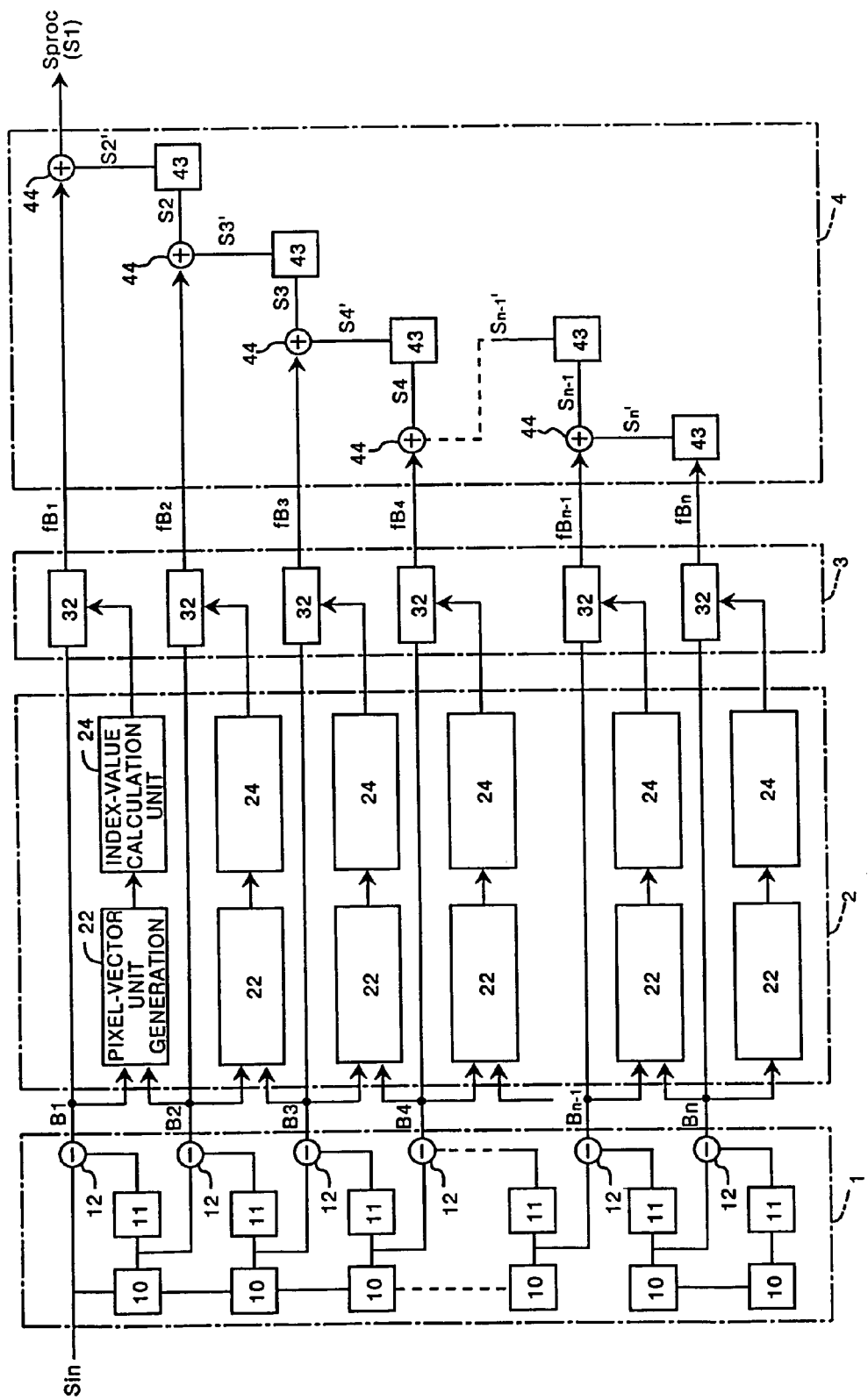
FIG. 5 is a block diagram illustrating details of a construction of the noise suppressing apparatus 100 as the first embodiment of the present invention.

FIG. 5 is a block diagram illustrating details of a construction of the noise suppressing apparatus 100.

The index-value obtaining unit 2 in the noise suppressing apparatus 100 of FIG. 5 comprises for each of the plurality of band-limited image signals Bk a pixel-vector generation unit 22 and an index-value calculation unit 24. The pixel-vector generation unit 22 corresponding to a resolution level generates a pixel vector at each pixel of a band-limited image represented by the corresponding band-limited image signal Bk, as an example of the aforementioned first (or second) evaluation value in the sixth aspect of the present invention. The index-value calculation unit 24 corresponding to a resolution level obtains at least one of a degree C of edge confidence, an index E of pixel energy, and an edge orientation, which are examples of the at least one index value in the sixth to eighth aspects of the present invention, for each pixel of the band-limited image, based on the length and/or orientation of the pixel vector generated by the pixel-vector generation unit 22 corresponding to the same resolution level.

The noise-suppression processing unit 3 in the noise suppressing apparatus 100 comprises a suppression processing unit 32 for each of the plurality of band-limited image signals Bk. The suppression processing unit 32 corresponding to a resolution level performs on the corresponding band-limited image signal Bk processing for suppressing noise included in the band-limited image signal Bk, based on the at least one index value output from the index-value calculation unit 24 corresponding to the same resolution level.

According to the noise suppression processing in the present embodiment, a line (edge) signal is smoothed along the orientation of the line (edge), and isolated noise is two-dimensionally smoothed. The most characteristic feature of the noise suppression processing is that a smooth edge is obtained by the smoothing operation of the line (edge) signal, and information necessary for the smoothing operation is represented in only a vector or tensor form. In the examples disclosed in this specification, the double-angle (D-A) representation is used as a vector representation form.

The D-A representation of a vector is a technique for representing a line (edge) signal, and advantageous in that the degree of confidence of a line (edge) signal can be obtained by only calculating a neighborhood average of information in the D-A representation. This feature is explained below with reference to FIGS. 6A to 6C.

Figure 6A:
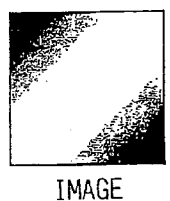
FIG. 6A is a diagram illustrating an example of an image.
Figure 6B:
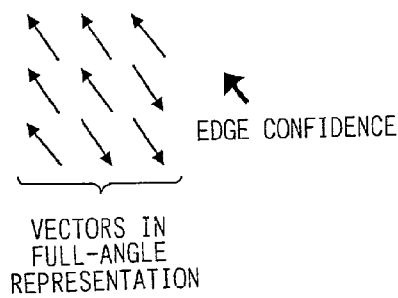
FIG. 6B is a diagram illustrating the density vectors obtained from the image of FIG. 6A in the full-angle (F-A) representation.

FIG. 6A shows an example of an image. When density vectors are calculated from an image signal representing the image of FIG. 6A, the density vectors are represented as illustrated in FIG. 6B in the full-angle (F-A) representation, which is an example of normal vector representations. That is, the orientations of the vectors on the respective sides of the boundary are opposite, where the low-density area in the image of FIG. 6A corresponds to the boundary. On the other hand, when the density vectors are represented in the D-A representation, the orientations of the vectors on both sides of the boundary are identical as illustrated in FIG. 6C since the angle values of the vectors are doubled in the D-A representation.

Figure 6C:
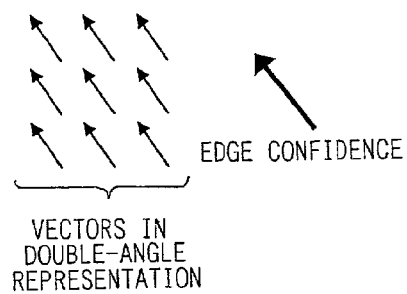
FIG. 6C is a diagram illustrating the density vectors obtained from the image of FIG. 6A in the double-angle (D-A) representation.

In addition, the degrees C of edge confidence of the above vectors are obtained by the neighborhood average in the F-A and D-A representations as respectively indicated with the bold arrows in FIGS. 6B and 6C. That is, the degree C of edge confidence obtained in the F-A representation is considerably smaller than the degree C of edge confidence obtained in the D-A representation. Although not shown, it will be easily understood that the confidence of noise also becomes small since vectors surrounding a vector of interest have random orientations. Therefore, it is difficult to discriminate between noise and line information in the F-A representation.

Figure 7:
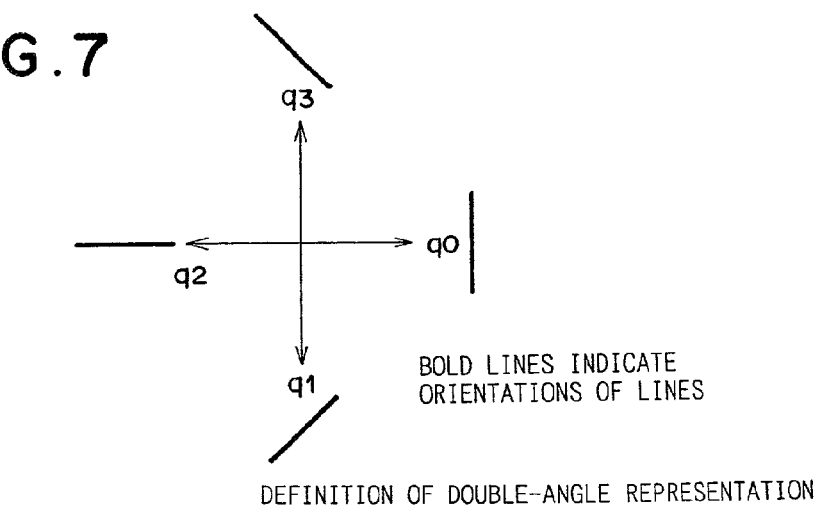
FIG. 7 is a diagram illustrating four directional components, corresponding to typical four line orientations, of vectors in the D-A representation.
Figure 8A:
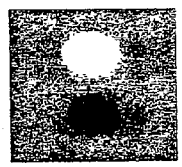
FIGS. 8A to 8D are diagrams respectively illustrating four two-dimensional filters for use in calculation of the four directional components q0 to q3.
Figure 8B:
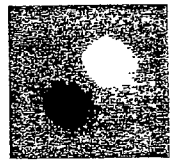
Figure 8C:
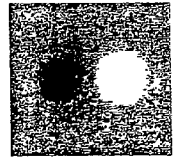
Figure 8D:
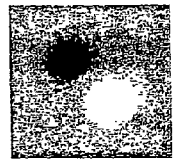

On the other hand, in the D-A representation, vectors indicating line (edge) orientations can be defined as illustrated in FIG. 7, in which q0 to q3 each indicate the magnitude of a directional component at a pixel of interest. When the magnitudes of two orthogonal directional components at a pixel are identical, e.g., when the pixel is located at a point of intersection of two lines, the output in the D-A representation becomes small. When two orthogonal directional components at a pixel have different magnitudes, the orientation corresponding to the greater magnitude becomes a main orientation at the pixel. Therefore, when the four directional components q0 to q3 of a vector at each pixel are obtained, the vector can be represented in the D-A representation.

Calculation of Directional Components

Details of operations for obtaining the directional components q0 to q3 are explained below.

TABLE 1

| Filter Coefficients for 5 × 5 q0 Filter | | | | |
|---|---|---|---|---|
| 0.0012 | 0.0211 | 0.0577 | 0.0211 | 0.0012 |
| 0.0053 | 0.1389 | 0.6093 | 0.1389 | 0.0053 |
| 0.0000 | 0.0000 | 0.0000 | −0.0000 | −0.0000 |
| −0.0053 | −0.1389 | −0.6093 | −0.1389 | −0.0053 |
| −0.0012 | −0.0211 | −0.0577 | −0.0211 | −0.0012 |

The band-limited image signals used for calculation of the directional components q0 to q3 are Laplacian signals generated by the Laplacian pyramid decomposition. The four directional components q0 to q3 are calculated by convolution of the Laplacian signals with the four two-dimensional filters, for example, as illustrated in FIGS. 8A to 8D. Table 1 shows examples of filter coefficients of a 5×5 q0 filter. Since each of the Laplacian signals can become positive or negative, and each of the filter coefficients can be positive or negative, absolute values of the convolution products are used for calculation of the directional components.

Each of the above-mentioned four two-dimensional filters is a kind of differential filter. Therefore, in the case where a second-derivative signal such as a Laplacian signal is convoluted with each of the four two-dimensional filters, the output of the filter does not become great in regions in which the gradient of the second-derivative signal is not great, even when the second-derivative signal per se is great in the regions. This feature is explained below with reference to FIG. 9.

FIG. 9 is a diagram illustrating a relationship between a Laplacian signal and an output of a first-derivative filter (the absolute value of the first derivative of the Laplacian signal). In FIG. 9, the point a of the Laplacian signal corresponds to a portion of an edge region, and the Laplacian signal is maximized at the point a. However, since the gradient of the Laplacian signal at the point a is zero, the output of the first derivative corresponding to the point a becomes zero.

In addition, the gradient of the Laplacian signal has a substantial amount at the point c, which is a boundary point between the edge region and a non-edge region. Therefore, the output of the first derivative corresponding to the point c becomes grater than the output of the first derivative corresponding to the point a. This tendency is strengthened when the mask size is increased. However, when the mask size is increased, trackability of very small edges decreases, and therefore sharpness of images of the very small edges decreases.

Thus, a small mask size is preferable when the input image signal does not include noise, for example, when the input image signal represents an artificially produced pattern image. However, usually, the input image signal represents a non-artificial image, and noise exists in the entire image in varying degrees. Therefore, first derivatives generated by using filters having a small mask size are strongly affected by noise.

The above circumstances can be a cause of image quality degradation when an adaptive filter which operates based on pixel energy (i.e., an average of the directional components q0 to q3) is used.

Nevertheless, when the amount of noise can be estimated, it is possible to optimize the filter by setting the mask size according to the amount of noise, or setting filter coefficients so as to substantially achieve the effect of the setting of the mask size. For example, when the input image is a radiographic image, as in the present embodiment, an X-ray dose and an amount of noise can be estimated from the S value (indicating the reading sensitivity) and the L value (indicating the latitude), and an optimum set of filter coefficients can be calculated. The S value and the L value are explained, for example, in U.S. Pat. No. 5,046,147 corresponding to Japanese Unexamined Patent Publication No. 2(1990)-108175.

Specifically, a neighborhood average of each of the vector components q0 to q3 at each pixel is obtained, for example, by using one of isotropic two-dimensional filters illustrated in FIGS. 10A to 10C.

When the mask size of the two-dimensional filter is varied, the smoothing level of the vector component varies. The smoothing level is reflected on the edge confidence and the pixel energy, and the influence of the smoothing level on the final image is relatively great. When the mask size is increased, noise and relatively large edges can be discriminated with high accuracy, and small edges are likely to be regarded as noise. Therefore, smoothing with a large mask size is effective when the input image does not include fine structures as a radiographic image of a chest of a child. On the other hand, since bone images such as an image of a foot includes complex fine structures such as trabecula, fine signals indicating the complex fine structures cannot be recognized when the smoothing level is raised. Therefore, a small mask size is used for images including fine structures.

As proposed in Japanese Unexamined Patent Publication No. 2000-306089 (corresponding to U.S. Ser. No. 09/505, 768)(now U.S. Pat. No. 6,771,793), the above neighborhood average can be modified by using vector components in a lower resolution image which has a lower resolution than the image from which the above neighborhood average is obtained. Researchers including the inventor of the present patent application have found the following characteristics in noise suppression using vector averages calculated from band-limited image signals.

(i) When the amount of noise included in the input image is small, e.g., when an X-ray exposure dose with which the input image has been produced is high, the signal-to-noise ratio (SNR) is high. Therefore, vector components obtained without use of the lower resolution signals can more faithfully follow fine signals representing fine structures in the input image than vector components modified with the lower resolution signals. That is, the edge degradation is less likely to occur when the vector components are obtained without use of the lower resolution signals.

(ii) When the amount of noise included in the input image is great, the signal-to-noise ratio is low. In this case, when an average of a vector calculated from a band-limited image signal in a frequency band (corresponding to at a resolution level) of interest and another vector calculated based on image information in a lower-frequency band (corresponding to a lower resolution level) is used, the average of the vectors can more faithfully follow relatively large signals which are not buried in the noise in the input image, since the signal-to-noise ratio of the image information in the lower-frequency band is better than the signal-to-noise ratio of the band-limited image signal in the frequency band of interest. Thus, noise can be effectively suppressed when the above average of the vectors is used.

Thus, in order to improve image quality, it is important to change the manner of noise suppression according to the amount of noise included in the input image.

For example, the above average of vectors can be calculated in accordance with the equation, $$AV = f(x) \times A + (1 - f(x)) \times B, \quad (3)$$

where A is a neighborhood average of vectors (vector average) calculated from a band-limited image signal in a frequency band of interest, B is another neighborhood average of vectors calculated based on image information in a lower frequency band, x represents an X-ray dose, and f(x) is a function of the X-ray dose x, and represents a weight of the neighborhood-averaged vector A in the weighted average AV. In order to obtain the neighborhood average B of vectors based on the image information in the lower frequency band, for example, the isotropic filter as illustrated in FIGS. 10B or 10C may be used.

In addition, in radiography, noise becomes dominant where the transmitted radiation dose is low. Therefore, the amount of noise included in the input image can be roughly estimated from the transmitted radiation dose.

The amount of noise included in the input image can be estimated by using various types of information which can directly or indirectly indicate the amount of noise included in the input image. For example, the following items can be used for estimating the amount of noise:

(a) The radiographed region or the menu of radiography
(b) The S or L value indicating a normalization condition (EDR condition)
(c) The signal values (density values) of the image
(d) The age of a patient or the condition of radiography When the above item (a) is used, for example, a low-dose menu, a child menu, and the like may be provided, and the weights of the aforementioned neighborhood-averaged vectors A and B in the weighted average AV can be changed according to a selected one of the menu.

When the above item (b) is used, it is possible to use as the function f(x) in the equation (3) a function which increases with decrease in the S value (corresponding to increase in the X-ray dose). For example, it is preferable to define the function f(x) by the following set of equations (4), although the function f(x) may be defined differently.

$$\left.\begin{array}{l} f(x) = 1.0 \text{ when } S < 100 \\ f(x) = (2000 - S)/1900 \text{ when } 100 \leq S \leq 2000 \\ f(x) = 0.0 \text{ when } S > 2000 \end{array}\right\} \quad (4)$$

Since the density value of each pixel of an image corresponds to the X-ray exposure at the pixel (for example, on a stimulable phosphor sheet), the relative amount of the X-ray exposure dose can be indicated by using the signal value (density value) of each pixel. Therefore, when the above item (c) is used, it is preferable to define the function f(x) by the following set of equations (5).

$$\left.\begin{array}{l} x = S \times 10^{(-L \times QL/1024)} \\ f(x) = 1.0 \text{ when } x < 100 \\ f(x) = (2000 - x)/1900 \text{ when } 100 \leq x \leq 2000 \\ f(x) = 0.0 \text{ when } x > 2000 \end{array}\right\} \quad (5)$$

In the set of equation (5), QL denotes a signal value, and x denotes a relative amount of the X-ray dose.

Alternatively, the set of equations (5) may be modified so that the function f(x) satisfies $0.5 \leq f(x) < 1.0$, instead of $0 \leq f(x) \leq 1.0$. That is, in the case where the signal values (density values) of the image are used for estimating the amount of noise included in the input image, the signal value of each pixel is referred to when the above weighted average AV of neighborhood-averaged vectors A and B is calculated, the relative amount of the X-ray exposure dose is estimated in accordance with the first equation of the set of equations (5), and the weights of the neighborhood-averaged vectors A and B in the weighted average AV are determined in accordance with the function f(x) defined in the other equations in the set of equations (5). Then, the above weighted average AV of vectors A and B is calculated by using the determined weights of the neighborhood-averaged vectors A and B.

Calculation of Index Values

Details of calculation of the index values used for noise suppression are explained below.

First, the orientations and lengths of a primary vector (ex1, ey1) and a secondary vector (ex2, ey2) are calculated by using the four vector components q0 to q3. Since each vector component is obtained in the D-A (double-angle) representation as illustrated in FIG. 7, the length V1 of the primary vector is calculated in accordance with equations (6), and the unit-vector components ex1 and ey1 of the primary vector are calculated in accordance with the equations (7).

$$\left.\begin{array}{l} Z1 = q0 - q2 \\ Z2 = q1 - q3 \\ V1 = (z1^2 + z2^2)^{1/2} \end{array}\right\} \quad (6)$$

$$\left.\begin{array}{l} ex1 = z1/V1 \\ ey1 = z2/V1 \end{array}\right\} \quad (7)$$

Since the secondary vector is perpendicular to the primary vector in the full-angle representation, the orientation of the secondary vector is opposite to that of the primary vector in the D-A representation. Therefore, the unit-vector components ex2 and ey2 of the secondary vector are calculated in accordance with the equations (8).

$$ex2 = -ex1 \atop ey2 = -ey1 \} \quad (8)$$

In addition, the amount of pixel energy Ve at each pixel is defined as an average of the four vector components q0 to q3 in accordance with the equations (9).

$$Ve=(q0+q1+q2+q3)/4 \quad (9)$$

Further, the length V2 of the secondary vector can be calculated from the ratio of the pixel energy Ve and the length V1 of the primary vector in accordance with the equations (10).

$$V2=(1-V1/Ve)\times V1 \quad (10)$$

Thus, information on the primary and secondary vectors is obtained as above by using the neighborhood averages of the four vector components q0 to q3 and the estimated amount of noise included in the input image.

Next, by using the above information on the primary and secondary vectors, the degree C of edge confidence, the index E of pixel energy, and a smoothing direction D of the anisotropic filter are calculated as examples of the aforementioned at least one index value which indicates a degree of noise suppression, in accordance with the following equations (11) to (13).

That is, the index E of pixel energy is calculated in accordance with the set of equations (11) by using a predetermined threshold value Th.

$$\begin{aligned} E &= (Ve/Th)^2/2 \text{ when } Ve < Th \\ E &= \{1-(2-Ve/Th)^2\}/2 \text{ when } Th \le Ve < 2\times Th \\ E &= 1.0 \text{ when } 2\times Th \le Ve \end{aligned} \} \quad (11)$$

That is, the index E of pixel energy is in the range, $0.0 \le E \le 1.0$.

In addition, the degree C of edge confidence is calculated from the lengths V1 and V2 of the primary and secondary vectors in accordance with the equation (12).

$$C=(V1-V2)/V1 \quad (12)$$

That is, the degree C of edge confidence is in the range, $0.0 \le C \le 1.0$.

Further, an angle θ, which indicates the smoothing direction of the anisotropic filter as a continuous value, is calculated from the unit-vector components of the secondary vector in accordance with the first and second equations in the set of equations (13), and a quantized smoothing direction D of the anisotropic filter is obtained from the continuous angle θ by the third equation g(θ) in the set of equations (13). The function g(θ) converts the continuous angle θ into one of 32 discrete angle values. That is, the smoothing direction D is in the range, $0 \le D \le 31$.

$$\begin{aligned} \theta &= \cos^{-1}(ex2) \text{ when } ey2 > 0 \\ \theta &= \cos^{-1}(-ex2) \text{ when } ey2 \le 0 \\ D &= g(\theta) \end{aligned} \} \quad (13)$$

The degree C of edge confidence indicates a degree of likelihood that the pixel constitutes an edge (line), and the index E of pixel energy indicates a degree of likelihood that the pixel constitutes a true signal, not noise. Examples of recognition of a line, a point of intersection, an end point, and noise by the aforementioned adaptive filter based on the degree C of edge confidence and the index E of pixel energy are indicated in FIGS. 11A to 11D.

Next, smoothing processing using an anisotropic filter and adaptive filtering are performed on each band-limited image signal (Laplacian signal) at each pixel based on the degree C of edge confidence, the index E of pixel energy, and the smoothing direction D, which are obtained as above from the information on the two orthogonal vectors.

Anisotropic Filter

In the present embodiment, smoothing processing is performed by using an anisotropic filter which is oriented along the line recognized based on the degree C of edge confidence. That is, the two-dimensional anisotropic spatial filter (orientation-dependent filter) smoothes the Laplacian signal along the orientation of the primary vector. The coefficients of the anisotropic filter can be set to have a shape, for example, as illustrated in FIGS. 12A to 12E, 13A to 13E, and 14A to 14E. Since noise in a noisy image is also superimposed on edge signals, the anisotropic filter as above is used for suppressing noise on an edge without reducing edge contrast.

Figures 12A, 12B, 12C, 12D, 12E:
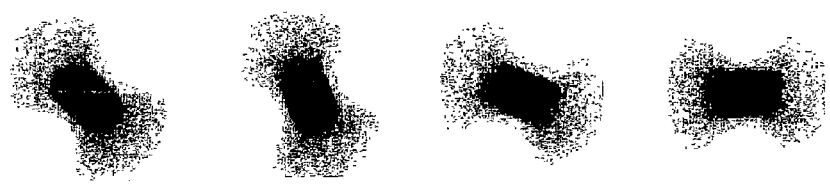
FIGS. 12A to 12E, 13A to 13E, and 14A to 14E are diagrams respectively illustrating examples of anisotropic filters having various characteristics.
Figures 13A, 13B, 13C, 13D, 13E:
Figures 14A, 14B, 14C, 14D, 14E:

In FIGS. 12A to 12E, 13A to 13E, and 14A to 14E, greater coefficients are indicated with higher density. For example, the filters illustrated in FIGS. 12A, 13A, and 14A are arranged for performing smoothing processing in the vertical direction. Although the smoothing capability is increased by increase in the center angle φ, smoothing of the edge signal is enhanced by the increase in the center angle φ. In addition, although the smoothing capability is also increased by increase in the mask size, edge degradation is enhanced by the increase in the mask size. In other words, when the mask size is small, the edge can be preserved while the smoothing capability is small. For example, the mask sizes of the anisotropic filters illustrated in FIGS. 12A to 12E are respectively greater than the mask sizes of the corresponding anisotropic filters illustrated in FIGS. 13A to 13E, and the mask sizes of the anisotropic filters illustrated in FIGS. 13A to 13E are respectively greater than the mask sizes of the corresponding anisotropic filters illustrated in FIGS. 14A to 14E.

When two-dimensional anisotropic filters as described above are used, it is possible to perform smoothing processing along the vector orientations. That is, noise on edges can be suppressed or eliminated while preserving the edges. Researchers including the inventor of the present patent application have found that the optimum extent of an effective area (mask size) of the anisotropic filter and the optimum degree of directionality (center angle) of the anisotropic filter vary with the amount of noise included in the input image, as described below. That is, in order to suppress or eliminate noise on an edge while preserving the edge, it is important to adaptively change the characteristics of the anisotropic filter according to the amount of noise included in the input image. Researchers including the inventor of the present patent application have found the following characteristics:

(i) When the amount of noise included in the input image is small, e.g., when an X-ray exposure dose with which the input image has been produced is high, it is preferable to use a filter which has a small effective area (mask size) and a small center angle so that fine signals can be followed more faithfully.

(ii) When the amount of noise included in the input image is great, higher smoothing capability is required. If the filter which has a small effective area (mask size) and a small center angle is used for the noisy image, artifacts are produced by a portion of noise ranging along the orientation of the vector.

As mentioned before, in radiography, the amount of noise included in the input image can be roughly estimated from the transmitted radiation dose, and the following items can be used for estimating the amount of noise included in the input image:

(a) The radiographed region or the menu of radiography
(b) The S or L value indicating a normalization condition (EDR condition)
(c) The signal values (density values) of the image
(d) The degree C of edge confidence
(e) The age of a patient or the condition of radiography Similar to the function f(x) used for determining the weights in the aforementioned weighted average of the neighborhood-averaged vectors, a function h(x) of an X-ray exposure dose is defined so that the characteristics of the anisotropic filter can be changed based on the value of the function h(x).

When the above item (a) is used, for example, a low-dose menu, a child menu, and the like may be provided, and it is preferable to determine the value of the function h(x) in advance for each menu.

When the above item (b) is used, it is possible to define as the function h(x) corresponding to the X-ray dose a function which increases with decrease in the S value (corresponding to increase in the X-ray dose). For example, it is preferable to define the function h(x) in accordance with the following set of equations (14), although the function h(x) may be defined differently.

$$\left.\begin{array}{ll} h(x) = 10 - 3 \times \log S & \text{when } 10 - 3 \times \log S \geq 1 \\ h(x) = 1 & \text{when } 10 - 3 \times \log S < 1 \end{array}\right\} \quad (14)$$

Since the density value of each pixel of the image corresponds to the X-ray exposure at the pixel (for example, on a stimulable phosphor sheet), the relative amount of the X-ray exposure dose can be indicated by using the signal value (density value) of each pixel. Therefore, when the above item (c) is used, it is preferable to define the function h(x) by the following set of equations (15).

$$\left.\begin{array}{l} x = S \times 10^{(-L \times QL/1024)} \\ h(x) = 10 - 3 \times \log x \quad \text{when } 10 - 3 \times \log x \geq 1 \\ h(x) = 1 \quad \text{when } 10 - 3 \times \log x < 1 \end{array}\right\} \quad (15)$$

In the set of equations (15), QL denotes a signal value, and x denotes a relative amount of the X-ray dose.

In this case, the signal value of each pixel is referred to when the anisotropic filter is used, the relative amount of the signal value is estimated in accordance with the first equation of the set of equations (15), and the value of the function h(x) is obtained based on the other equations in the set of equations (15). Then, the characteristics of the anisotropic filter can be adaptively changed based on the obtained value of the function h(x). For example, when the signal value is small (i.e., the X-ray exposure dose is low), the center angle and the mask size of the anisotropic filter are increased, and therefore the smoothing capability is increased. Conversely, when the signal value is great (i.e., the X-ray exposure dose is high), the center angle and the mask size of the anisotropic filter are decreased, and therefore the edge degradation can be prevented.

As explained before, the degree C of edge confidence is obtained after the aforementioned weighted average of the neighborhood-averaged vectors is obtained, and each pixel is less likely to constitute noise when the degree C of edge confidence at the pixel is great. Conversely, the degrees C of edge confidence are small in noisy images. Therefore, the degree C of edge to confidence can also be used as an index for estimating the amount of noise included in the input image. That is, when the degree C of edge confidence is great, the center angle and the mask size of the anisotropic filter can be decreased. Conversely, when the degree C of edge confidence is small, the center angle and the mask size of the anisotropic filter can be increased. Thus, it is possible to concurrently realize the noise suppression and the edge sharpening.

Further, although anisotropic filters preserve edges, the anisotropic filters smooth points at which edges intersect. However, intersection points appearing on actual images are not ideal intersection points. That is, in the actual images, edges are not sharp, or do not intersect at the right angle. Therefore, intersection points appearing on actual images are not heavily smoothed.

Noise Suppression

As described above, the characteristics of the anisotropic filter are selected based on the smoothing direction D(θ) and the amount of noise included in the input image, and then the band-limited image signal Bk (Laplacian signal) corresponding to each resolution level is convoluted with the anisotropic filter having the selected characteristics so as to produce a convolution product AF (as an anisotropic-filtered signal). In addition, the noise-suppression processing unit 3 calculates a weighted sum of the above convolution product AF and the band-limited image signal (Laplacian signal) Bk by using the index E of pixel energy and the degree C of edge confidence so as to obtain a processed band-limited image signal fBk (k=1 to n) for each pixel of the band-limited image represented by the band-limited image signal (Laplacian signal) Bk, where noise components in the processed band-limited image signal fBk is suppressed. The weighted sum of the convolution product AF and the band-limited image signal Bk can be defined differently depending on whether each pixel at which the degree C of edge confidence is nearly equal to one and the index E of pixel energy is very small (for example, as illustrated in FIG. 11B) is regarded as a constituent of a true edge signal or noise.

When each pixel at which the degree C of edge confidence is nearly equal to one and the index E of pixel energy is very small (for example, as illustrated in FIG. 11B) is regarded as a constituent of a true signal, the processed band-limited image signal fBk can be calculated in accordance with the following equation (16), $$Proc = C \times AF + E \times (1-C) \times Org, \quad (16)$$

where Proc represents the processed band-limited image signal fBk, and Org represents the (original) band-limited image signal (Laplacian signal) Bk.

In the case where the processed band-limited image signal fBk is obtained in accordance with the equation (16), the anisotropic-filtered signal AF (in the first term on the right side of the equation (16)) becomes dominant when the degree C of edge confidence is nearly equal to one. That is, when the degree C of edge confidence is nearly equal to one, the pixel is regarded as a constituent of an edge. In addition, when the index E of pixel energy is very small, the original signal Org (i.e., the Laplacian signal Bk in the second term) is attenuated by the very small index E of pixel energy. Thus, noise and intersection points are separated from edges, i.e., components corresponding to noise and intersection points are eliminated from the processed band-limited image signal fBk (Proc).

When each pixel at which the degree C of edge confidence is nearly equal to one and the index E of pixel energy is very small is regarded as noise, the processed band-limited image signal fBk can be calculated in accordance with the following equation (17), $$Proc = E \times C \times AF + E \times (1-C) \times Org. \quad (17)$$

In the case where the processed band-limited image signal fBk is obtained in accordance with the equation (17), the anisotropic-filtered signal AF (in the first term on the right side of the equation (16)) can be attenuated by the index E of pixel energy even when the degree C of edge confidence is nearly equal to one. Thus, the noise is separated from edges, i.e., components corresponding to noise are eliminated from the processed band-limited image signal fBk (Proc). In addition, when both of the degree C of edge confidence and the index E of pixel energy are low, the original signal Org (i.e., the Laplacian signal Bk in the second term) is attenuated by the small index E of pixel energy. Thus, noise and intersection points are separated from edges, i.e., components corresponding to noise and intersection points are eliminated from the processed band-limited image signal fBk (Proc).

However, in the case where the processed band-limited image signal fBk (Proc) is calculated in accordance with the equation (16), noise can be eliminated from the processed band-limited image signal fBk (Proc) only when the signal-to-noise ratio (SNR) is high. That is, when the signal-to-noise ratio is low, noise cannot be eliminated from the processed band-limited image signal fBk (Proc). This is because the degree C of edge confidence at a pixel can become high in the low-SNR situation even when the pixel represents noise.

On the other hand, in the case where the processed band-limited image signal fBk (Proc) is calculated in accordance with the equation (17), an artifact (local discontinuity caused by noise or an artificially produced edge which suddenly appears) is more likely to be produced when the signal-to-noise ratio decreases. In order to eliminate the artifact, the threshold value used in the calculation of the index E of pixel energy (i.e., the value Th in the equation (11)) is required to be raised. However, when the threshold value is raised, edges become unclear. This is because the indexes E of pixel energy of noise compete with the indexes E of pixel energy of true signals in the low-SNR situation, and this problem is inevitable when the pixel energy is used in discrimination between true signals and noise.

Further, the degree C of edge confidence of a pixel has a small value when the pixel constitutes a nonlinear signal representing an intersection point, an end point, or the like. Therefore, in order to discriminate between the nonlinear signal and noise, it is possible to determine whether each pixel corresponds to a true signal or noise by comparing the index E of pixel energy with a predetermined value. In practice, it is possible to determine the unlikelihood of noise as a continuous function by using an arbitrary nonlinear function. For example, the unlikelihood N of noise can be determined by using a nonlinear function of a threshold value TH and the index E of pixel energy, as indicated in the equation (18).

$$N = \frac{\exp(TH/E) - 1}{\exp(TH/E) + 1} \times 2 \times \frac{E}{TH} \quad (18)$$

In this case, it is preferable to replace the aforementioned equation (16) with the equation (19), and the aforementioned equation (17) with the equation (20).

$$Proc = C \times AF + N \times (1-C) \times Org \quad (19)$$

$$Proc = E \times C \times AF + N \times (1-C) \times Org \quad (20)$$

In the equation (18), the threshold value TH is a value determined based on an amount corresponding to an exposure dose. For example, when the amount corresponding to the exposure dose is a pixel value (i.e., a signal value at each pixel), the threshold value TH varies from pixel to pixel.

In addition, the unlikelihood N of noise defined by the equation (18) asymptotically approaches 1.0 when the ratio of the index E of pixel energy to the threshold value TH greatly increases. For example, when the index E of pixel energy is sufficiently greater than the threshold value TH, the unlikelihood N of noise becomes nearly equal to one, and therefore the second terms in the equations (19) and (20) remain. However, when the index E of pixel energy is sufficiently smaller than the threshold value TH, the unlikelihood N of noise becomes nearly equal to zero, and therefore the second terms in the equations (19) and (20) are suppressed. Since the degree C of edge confidence of the pixel constituting a nonlinear signal is small, the second terms in the equations (19) and (20) are also suppressed. Therefore, when the index E of pixel energy is sufficiently smaller than the threshold value TH, the processed band-limited image signal Proc defined by each of the equations (19) and (20) becomes nearly zero.

Reconstruction of Image

After the noise suppression processing is performed on the band-limited image signals Bk, i.e., the processed band-limited image signals fBk (Proc) (k=1 to n) are obtained, the image reconstruction unit 4 makes a Laplacian reconstruction as an inverse multiresolution transformation so as to produce a processed image signal Sproc which represents an image in which noise components are suppressed.

Figure 15:
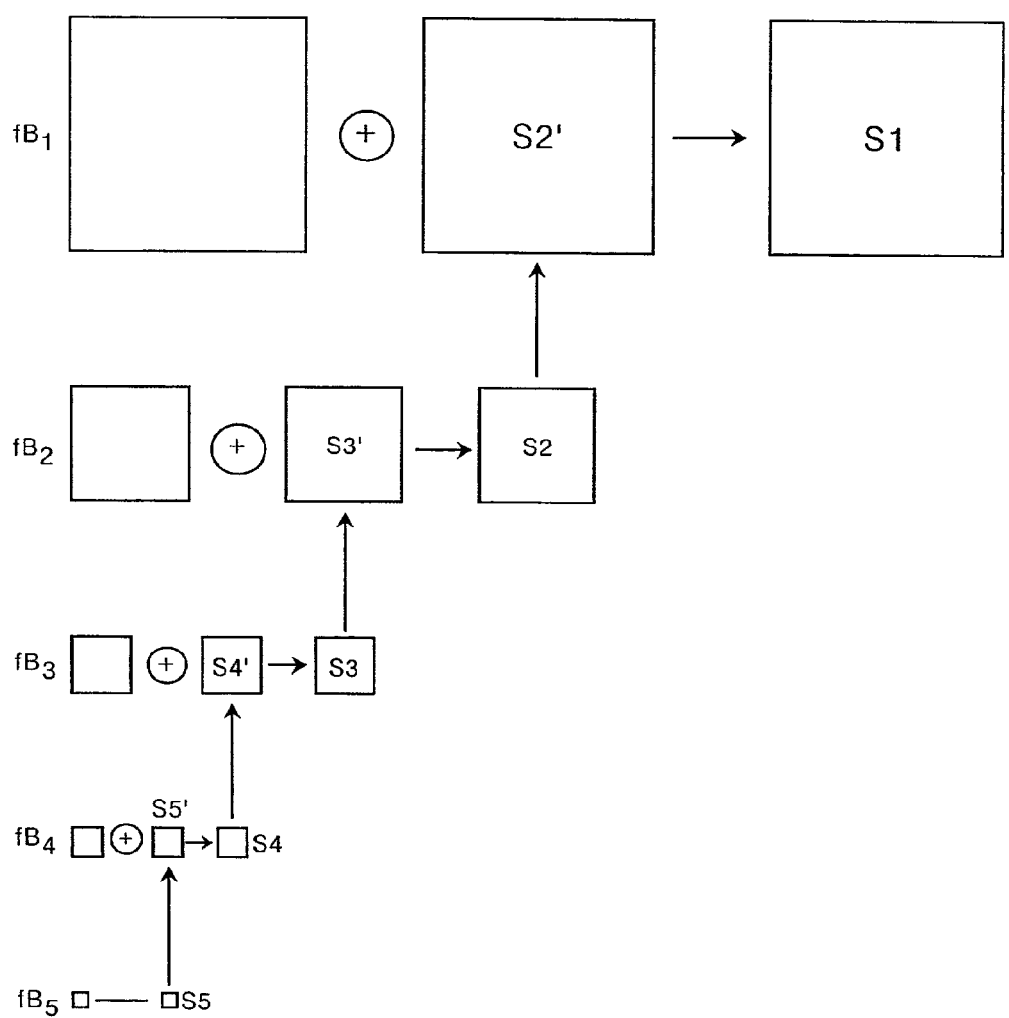
FIG. 15 is a diagram schematically illustrating an example of the operation for performing the Laplacian reconstruction.

As illustrated in FIG. 5, the image reconstruction unit 4 comprises an interpolation processing unit 43 and an adder 44 corresponding to each resolution level. The interpolation processing unit 43 corresponding to the lowest resolution level performs interpolation processing on the processed band-limited image signal fBn at the lowest resolution level so as to obtain an interpolated (magnified) image signal Sn' at the lowest resolution level. The adder 44 corresponding to the second lowest resolution level obtains a sum of the processed band-limited image signal fBn−1 (Proc) at the second lowest resolution level and the interpolated (magnified) image signal Sn' from the lowest resolution level so as to obtain an added image signal Sn−1. Thereafter, the interpolation processing unit 43 corresponding to each of the other resolution levels performs interpolation processing on an added image signal Sk at the resolution level so as to obtain an interpolated (magnified) image signal Sk' at the resolution level. Then, the adder 44 at the one-level higher resolution level obtains a sum of the processed band-limited image signal fBk (Proc) at the one-level higher resolution level and the interpolated (magnified) image signal Sk+1' so as to obtain an added image signal Sk at the one-level higher resolution level. Thus, finally, the adder 44 at the highest resolution level outputs the processed image signal Sproc (as the added image signal S1). An example of the operation for the Laplacian reconstruction is schematically illustrated in FIG. 15 for the case where n=5.

When parameters in the adaptive filter and the like are appropriately adjusted, and an image is produced with a low exposure dose and processed as above in the present embodiment, the processed image has an appearance which is similar to the appearances of slightly unsharped images of high-frequency components produced with a medium exposure dose by conventional techniques. Since the weights in the weighted average of the neighborhood averages of vectors at a resolution level of interest and a lower resolution level are controlled based on the X-ray dose or doses in the input image, fine-edge-oriented noise suppression is performed in areas of an image which are exposed with a high X-ray dose, and large-edge-oriented noise suppression is performed in areas of the image which are exposed with a low X-ray dose. Therefore, noise can be effectively suppressed or eliminated in the entire image, edge degradation, which can be caused by noise suppression in a noisy image, can be reduced, and variations in image quality caused by variations in the exposure dose can be suppressed. In other words, even when the amount of noise included in the image varies due to variations in the exposure dose, the noise suppressing apparatus 100 can effectively suppress the noise in the image, reduce artifacts such as an arabesque pattern, and make the image more natural. In addition, degradation of fine signals can be reduced. Thus, it is possible to obtain high quality images by use of the noise suppressing apparatus 100.

Second Embodiment

Although, in the first embodiment, the noise-suppressed image signal is obtained from the plurality of noise-suppressed band-limited image signals by the inverse multiresolution transformation, an added noise component signal SH1 representing all of the noise components included in the input image may be obtained by using the multiple resolution signals, and subtracted from the input image signal Sin so as to obtain the noise-suppressed image signal, as disclosed in Japanese Unexamined Patent Publication No. 2001-057677 and the corresponding U.S. Ser. No. 09/592, 602(now U.S. Pat. No. 6,754,398), the contents of which are incorporated in this specification by reference. Details of a construction of a noise suppressing apparatus which realizes the above operations for obtaining the noise-suppressed image signal are illustrated in FIG. 16 as the second embodiment of the present invention.

Figure 16:
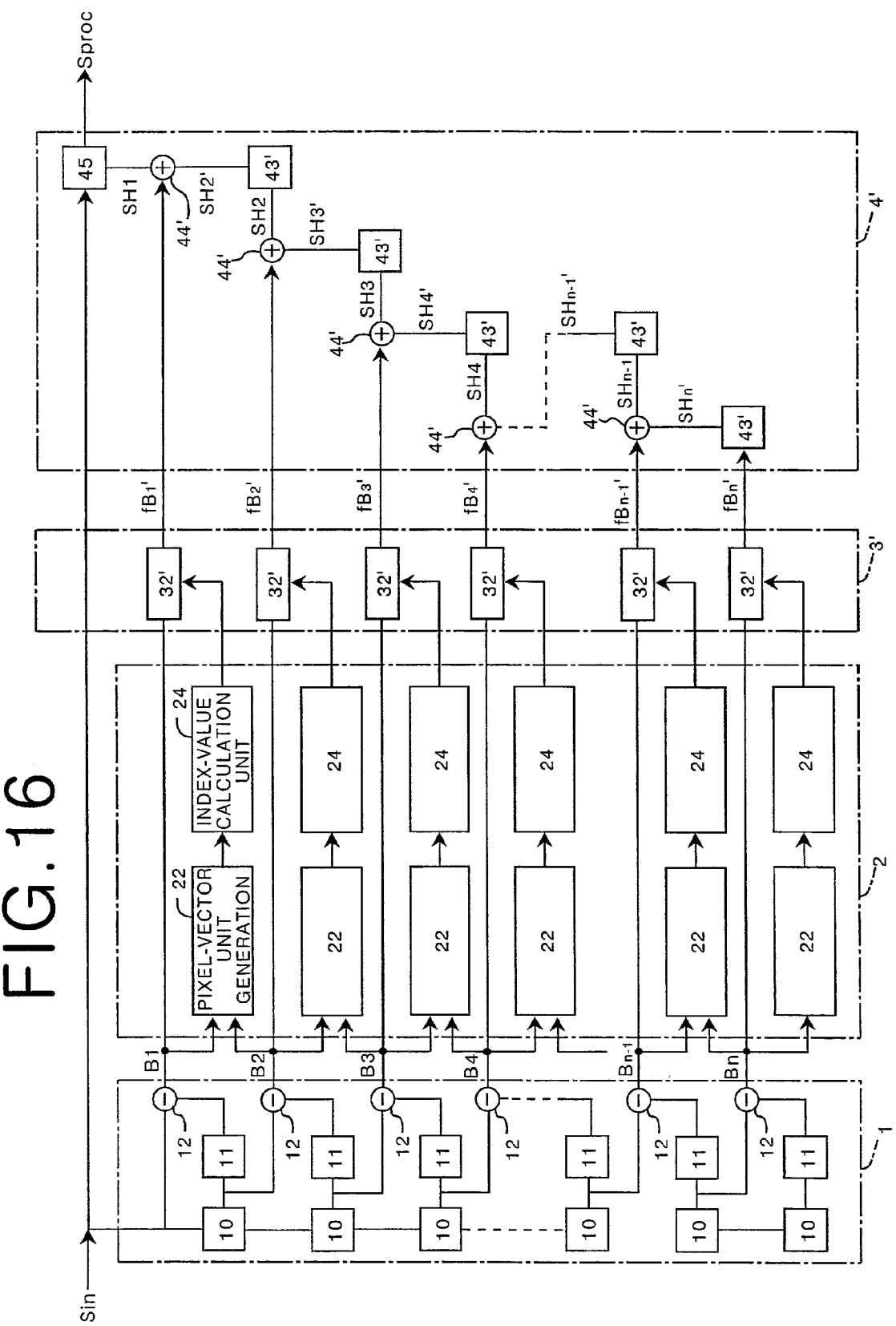
FIG. 16 is a diagram illustrating details of another construction of the noise suppressing apparatus as the second embodiment of the present invention which realizes operations for obtaining a noise-suppressed image.

In the construction of FIG. 16, a noise extraction unit 3' and an image reconstruction unit 4' are provided instead of the noise-suppression processing unit 3 and the image reconstruction unit 4 in the construction of FIG. 5. The noise extraction unit 3' comprises a noise-component extraction unit 32' at each resolution level, instead of the suppression processing unit 32 in the construction of FIG. 5, and the image reconstruction unit 4' comprises a noise subtraction unit 45 in addition to an interpolation processing unit 43' and an adder 44' provided at each resolution level.

The noise-component extraction unit 32' provided at each resolution level in the noise extraction unit 3' extracts a noise component signal fBk' from the processed band-limited image signal fBk. In the image reconstruction unit 4', the interpolation processing unit 43' corresponding to the lowest resolution level performs interpolation processing on the noise component signal fBn' at the lowest resolution level so as to obtain a magnified noise component signal SHn' having an increased number of pixels. Then, the magnified noise component signal SHn' is added to the noise component signal fBn−1' by the adder 44' so as to produce an added noise component signal SHn−1 at the second lowest resolution level. Thereafter, the interpolation processing unit 43' corresponding to each of the other resolution levels performs interpolation processing on an added noise component signal SHk at the resolution level so as to obtain a magnified noise component signal SHk' having an increased number of pixels. Then, the magnified noise component signal SHk' is added to the noise component signal fBk−1' at the one-level higher resolution level by the adder 44' at the one-level higher resolution level so as to produce an added noise component signal SHk−1 at the one-level higher resolution level. Thus, finally, the adder 44' corresponding to the highest resolution level outputs an added noise component signal SH1. The noise subtraction unit 45 subtracts the added noise component signal SH1 from the input image signal Sin so as to obtain the noise-suppressed image signal Sproc.

Variations and Modifications

The present invention is not limited to the exact constructions and applications shown and described. For example, the following modifications or changes are possible.

(i) Although, in the described embodiments, the band-limited image signals in respectively different frequency bands are generated from the input image signal Sin by the Laplacian pyramid decomposition, the band-limited image signals may be generated by the wavelet transformation as disclosed in Japanese Unexamined Patent Publication No. 6(1994)-274615, the contents of which are incorporated in this specification by reference.

(ii) In the described embodiments, the index values indicating the degree of noise suppression is obtained based on the vector information (the weighted average of neighborhood averages of the vectors), and filter processing is performed based on the index values, where the vector information is local information locally calculated from values of pixels in the neighborhood of each pixel of interest. Alternatively, a tensor average or the local variance obtained as disclosed in U.S. Pat. No. 5,461,655 may be used as the local information, instead of the above vector information. In the case where the local variance is used, when a first local variance corresponding to a first band-limited image signal at a first resolution level is calculated for a pixel of interest, a second local variance may be added to the first local variance according to information which indicates an exposure dose such as a menu or condition of radiography or an amount corresponding to the radiation dose, where the second local variance is calculated for the pixel of interest from a second band-limited image signal at a second resolution level which is lower than the first resolution level.

When the second local variance may be added to the first local variance, a weight of the second local variance in the addition may be changed according to the exposure dose at each location of the image, and an unlikelihood N of noise may be calculated so as to transform the original signal (band-limited image signal) Org into a processed band-limited image signal as Proc=N X Org.

(iii) In the smoothing processing, the filter coefficients or mask size of the (normal two-dimensional) isotropic spatial filter may be changed. The characteristics of the isotropic spatial filter may be changed based on the local variance of the detail image and information corresponding to the X-ray dose, where the local variance of the detail image can be obtained as disclosed in U.S. Pat. No. 5,461,655. However, edge degradation is likely to occur in the smoothing processing by changing the characteristics of the isotropic spatial filter. Therefore, the smoothing processing along the orientation of the edge by using the anisotropic spatial filter is more preferable than the smoothing by changing the characteristics of the isotropic spatial filter.

(iv) In the described embodiments, characteristics of the input image signal are calculated based on the information on the exposure dose after the plurality of band-limited image signals respectively carrying band-limited images in different frequency bands are produced, and the characteristics of the smoothing filter are adaptively changed based on the characteristics of the input image signal so as to smooth each band-limited image signal by using the smoothing filter. Alternatively, even when smoothing processing is performed on the input image signal per se, it is possible to adaptively change characteristics of a smoothing filter based on the characteristics of the input image signal. In this case, it is also possible to use the aforementioned techniques in which the characteristics of the input image signal are obtained by using local information such as the vector information as well as the information on the exposure dose.

(v) In the described embodiments, the index values indicating the degree of noise suppression are obtained from the image signal (particularly from the band-limited image signals), and the noise suppression processing is performed based on the index values so as to obtain an image in which noise is effectively suppressed regardless of the exposure dose. However, the index values which indicate the degree of suppression of noise components may be defined in any other way. For example, information indicating the exposure dose with which the input image has been produced can be used as the index values. In this case, the information indicating the exposure dose with which the input image has been produced may be obtained, for example, by using a photo timer or the like.

What is claimed is:

1. An apparatus for suppressing noise in an input image signal representing a radiographic image, comprising:
    a band-limited-image-signal generation unit which generates a plurality of band-limited image signals respectively representing a plurality of band-limited images belonging to a plurality of different frequency bands, based on said input image signal;
    an index-value obtaining unit which obtains at least one index value indicating a degree of suppression of said noise, based on information indicating an exposure dose with which said radiographic image has been produced; and
    a noise suppression unit which processes each of said plurality of band-limited image signals so as to suppress noise in each of said plurality of band-limited images based on said at least one index value,
    wherein said index-value obtaining unit obtains said at least one index value indicating the degree of suppression of the noise for each of said plurality of band-limited image signals,
    wherein said noise suppression unit processes each of said plurality of band-limited image signals so as to suppress the noise in each of said plurality of band-limited images based on said at least one index value obtained for said each of said plurality of band-limited image signals, and
    wherein said index-value obtaining unit obtains a first evaluation value from a first one of said plurality of band-limited image signals belonging to a first one of said plurality of different frequency bands and a second evaluation value from a second one of said plurality of band-limited image signals belonging to a second one of said plurality of different frequency bands which is lower than said first one of said plurality of different frequency bands, determines weights based on said information indicating the exposure dose with which the radiographic image has been produced, for use in a weighted sum of said first and second evaluation values, obtains said weighted sum, and obtains based on said weighted sum said at least one index value indicating the degree of suppression of the noise for said first one of said plurality of band- limited image signals.

2. An apparatus according to claim 1, wherein said index-value obtaining unit obtains each of said first and second evaluation values for each pixel of one of said plurality of band-limited images corresponding to said each of said first and second evaluation values, based on pixel values of said one of said plurality of band-limited images in a neighborhood of said each pixel.

3. An apparatus according to claim 1, wherein said index-value obtaining unit obtains as each of said first and second evaluation values a pixel vector at each pixel of one of said plurality of band-limited images corresponding to said each of said first and second evaluation values, and obtains said at least one index value based on at least one of a length and an orientation of said pixel vector.

4. An apparatus according to claim 3, wherein said index-value obtaining unit obtains as said at least one index value at least one of a degree of edge confidence, an amount of pixel energy, and a vector orientation.

5. An apparatus for suppressing noise in an input image signal representing a radiographic image, comprising:
    a band-limited-image-signal generation unit which generates a plurality of band-limited image signals respectively representing a plurality of band-limited images belonging to a plurality of different frequency bands, based on said input image signal;
    an index-value obtaining unit which obtains at least one index value indicating a degree of suppression of said noise, based on information indicating an exposure dose with which said radiographic image has been produced; and
    a noise suppression unit which processes each of said plurality of band-limited image signals so as to suppress noise in each of said plurality of band-limited images based on said at least one index value,
    wherein said noise suppression unit processes one of said plurality of band-limited image signals so as to generate a transformed image signal, and obtains a weighted sum of said one of said plurality of band-limited image signals and said transformed image signal by using weights determined based on said at least one index value.

6. An apparatus according to claim 5, wherein said index-value obtaining unit obtains a pixel vector at each pixel of one of said plurality of band-limited images, and said noise suppression unit arranges an orientation-dependent filter based on a length and an orientation of said pixel vector, and obtains said transformed image signal by convolution of pixel values in a neighborhood of said each pixel in said one of said plurality of band-limited images with said orientation-dependent filter.

7. An apparatus for suppressing noise in an input image signal representing a radiographic image, comprising:
a smoothing unit which processes said input image signal by using a smoothing filter so as to smooth said radiographic image; and
a characteristic calculation unit which obtains at least one first characteristic of said input image signal by calculation using a function based on first information indicating an exposure dose with which said radiographic image has been produced;
said smoothing unit adapts at least one second characteristic of the smoothing filter to said input image signal based on said at least one first characteristic, wherein the first information represents at least one of a S value, indicating a reading sensitivity, and an L value, indicating latitude, of the radiographic image.

8. A method for suppressing noise in an input image signal representing a radiographic image, said method comprising the steps of:
(a) obtaining at least one first characteristic of said input image signal by calculation using a function based on information indicating an exposure dose with which said radiographic image has been produced;
(b) adapting at least one second characteristic of a smoothing filter to said input image signal based on said at least one first characteristic; and
(c) processing said input image signal by using said smoothing filter so as to smooth said radiographic image, wherein the first information represents at least one of a S value indicating a reading sensitivity, and an L value, indicating latitude, of the radiographic image.

9. A method for suppressing noise in an input image signal representing a radiographic image, said method comprising the steps of:
(a) generating a plurality of band-limited image signals respectively representing a plurality of band-limited images belonging to a plurality of different frequency bands, based on said input image signal;
(b) obtaining at least one first characteristic of said input image signal by calculation using a function based on information indicating an exposure dose with which said radiographic image has been produced;
(c) adapting at least one second characteristic of a smoothing filter to said input image signal based on said at least one first characteristic; and
(d) processing said plurality of band-limited image signals by using said smoothing filter so as to smooth each of said plurality of band-limited images, wherein the first information represents at least one of a S value, indicating a reading sensitivity, and an L value, indicating latitude, of the radiographic image.

10. An apparatus for suppressing noise in an input image signal representing a radiographic image, comprising:
a band-limited-image-signal generation unit which generates a plurality of band-limited image signals respectively representing a plurality of band-limited images belonging to a plurality of different freciuency bands, based on said input image signal:
an index-value obtaining unit which obtains at least one index value indicating a degree of suppression of said noise, the at least one index value corresponding to a function based on information indicating an exposure dose with which said radiographic image has been produced: and
a noise suppression unit which processes each of said plurality of band-limited image signals so as to suppress noise in each of said plurality of band-limited images based on said at least one index value, wherein the first information represents at least one of a S value, indicating a reading sensitivity, and an L value, indicating latitude, of the radiographic image.

11. A method for suppressing noise in an input image signal representing a radiographic image, said method comprising the steps of:
(a) generating a plurality of band-limited image signals respectively representing a plurality of band-limited images belonging to a plurality of different frequency bands, based on said input image signal;
(b) obtaining at least one index value indicating a degree of suppression of said noise, the at least one index value corresponding a function based on information indicating an exposure dose with which said radiographic image has been produced; and
(c) processing each of said plurality of band-limited image signals so as to suppress noise in each of said plurality of band-limited images based on said at least one index value, wherein the first information represents at least one of a S value, indicating a reading sensitivity, and an L value, indicating latitude, of the radiographic image.

12. An apparatus for suppressing noise in an input image signal representing a radiographic image, comprising:
a smoothing unit which processes said input image signal by using a smoothing filter so as to smooth said radiographic image; and
a characteristic calculation unit which obtains at least one first characteristic of said input image signal by calculation using a function based on first information indicating an exposure dose with which said radiographic image has been produced;
said smoothing unit adapts at least one second characteristic of the smoothing filter to said input image signal based on said at least one first characteristic, wherein the first information represents one of a selected menu item of an apparatus used to obtain the radiographic image, an age of a subject in the radiographic image and information from a photo-timer used to obtain the radiographic image.

13. A method for suppressing noise in an input image signal representing a radiographic image, said method comprising the steps of:
(a) obtaining at least one first characteristic of said input image signal by calculation using a function based on information indicating an exposure dose with which said radiographic image has been produced;
(b) adapting at least one second characteristic of a smoothing filter to said input image signal based on said at least one first characteristic; and
(c) processing said input image signal by using said smoothing filter so as to smooth said radiographic image, wherein the first information represents one of a selected menu item of an apparatus used to obtain the radiographic image, an age of a subject in the radiographic image and information from a photo-timer used to obtain the radiographic image.

14. A method for suppressing noise in an input image signal representing a radiographic image, said method comprising the steps of:

(a) generating a plurality of band-limited image signals respectively representing a plurality of band-limited images belonging to a plurality of different frequency bands, based on said input image signal;

(b) obtaining at least one first characteristic of said input image signal by calculation using a function based on information indicating an exposure dose with which said radiographic image has been produced;

(c) adapting at least one second characteristic of a smoothing filter to said input image signal based on said at least one first characteristic; and (d) processing said plurality of band-limited image signals by using said smoothing filter so as to smooth each of said plurality of band-limited images, wherein the first information represents one of a selected menu item of an apparatus used to obtain the radiographic image, an age of a subject in the radiographic image and information from a photo-timer used to obtain the radiographic image.

15. An apparatus for suppressing noise in an input image signal representing a radiographic image, comprising:

a band-limited-image-signal generation unit which generates a plurality of band-limited image signals respectively representing a plurality of band-limited images belonging to a plurality of different frequency bands, based on said input image signal;

an index-value obtaining unit which obtains at least one index value indicating a degree of suppression of said noise, the at least one index value corresponding to a function based on information indicating an exposure dose with which said radiographic image has been produced; and a noise suppression unit which processes each of said plurality of band-limited image signals so as to suppress noise in each of said plurality of band-limited images based on said at least one index value, wherein the first information represents one of a selected menu item of an apparatus used to obtain the radiographic image, an age of a subject in the radiographic image and information from a photo-timer used to obtain the radiographic image.

16. A method for suppressing noise in an input image signal representing a radiographic image, said method comprising the steps of:

(a) generating a plurality of band-limited image signals respectively representing a plurality of band-limited images belonging to a plurality of different frequency bands, based on said input image signal;

(b) obtaining at least one index value indicating a degree of suppression of said noise, the at least one index value corresponding a function based on information indicating an exposure dose with which said radiographic image has been produced; and (c) processing each of said plurality of band-limited image signals so as to suppress noise in each of said plurality of band-limited images based on said at least one index value, wherein the first information represents one of a selected menu item of an apparatus used to obtain the radiographic image, an age of a subject in the radiographic image and information from a photo-timer used to obtain the radiographic image.

* * * * *